(12) United States Patent
LeCloux et al.

(10) Patent No.: US 8,529,796 B2
(45) Date of Patent: Sep. 10, 2013

(54) CHARGE TRANSPORT COMPOSITIONS AND ELECTRONIC DEVICES MADE WITH SUCH COMPOSITIONS

(75) Inventors: Daniel David LeCloux, Midland, MI (US); Eric Maurice Smith, Hockessin, DE (US); Ying Wang, Wilmington, DE (US); Norman Herron, Newark, DE (US); Mark A Guidry, Wilmington, DE (US); Nora Sabina Radu, Landenberg, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/617,717

(22) Filed: Sep. 14, 2012

(65) Prior Publication Data

US 2013/0009142 A1 Jan. 10, 2013

Related U.S. Application Data

(62) Division of application No. 13/029,458, filed on Feb. 17, 2011, now Pat. No. 8,293,139, which is a division of application No. 12/126,061, filed on May 23, 2008, now Pat. No. 7,914,706, which is a division of application No. 10/612,704, filed on Dec. 8, 2003, now Pat. No. 7,399,432.

(60) Provisional application No. 60/458,277, filed on Mar. 28, 2003.

(51) Int. Cl.
*H01B 1/00* (2006.01)
*C07D 241/36* (2006.01)
*H01L 29/08* (2006.01)
*H01J 1/62* (2006.01)

(52) U.S. Cl.
USPC .............. 252/500; 544/353; 257/40; 313/506

(58) Field of Classification Search
USPC ........... 252/500; 257/40; 313/504; 544/353
See application file for complete search history.

(56) References Cited

U.S. PATENT DOCUMENTS

| | | | |
|---|---|---|---|
| 3,423,427 A | 1/1969 | Cescon et al. | |
| 3,449,379 A | 6/1969 | Cescon et al. | |
| 3,615,481 A | 10/1971 | Looney | |
| 3,666,466 A | 5/1972 | Strilko | |
| 3,739,000 A | 6/1973 | Maggiulli et al. | |
| 4,140,529 A | 2/1979 | Pai et al. | |

(Continued)

FOREIGN PATENT DOCUMENTS

| | | |
|---|---|---|
| EP | 341859 A1 | 11/1989 |
| EP | 564224 A2 | 5/1997 |

(Continued)

OTHER PUBLICATIONS

Jandke et al., "Phenylquinoxaline Polymers and Low Molar Mass Glasses as Electron-Transport Materials in Organic Light-Emitting Diodes," Macromolecules, 31, pp. 6434-6443 (1998).*

(Continued)

*Primary Examiner* — Mark Kopec
*Assistant Examiner* — Jaison Thomas

(57) ABSTRACT

The present invention relates to charge transport compositions. The invention further relates to electronic devices in which there is at least one active layer comprising such charge transport compositions.

13 Claims, 18 Drawing Sheets

(56) References Cited

U.S. PATENT DOCUMENTS

| | | | |
|---|---|---|---|
| 4,304,829 | A | 12/1981 | Limburg et al. |
| 4,579,679 | A | 4/1986 | Papir |
| 4,853,090 | A | 8/1989 | Daniel et al. |
| 4,996,124 | A | 2/1991 | Buettner et al. |
| 5,077,142 | A | 12/1991 | Sakon et al. |
| 5,294,810 | A | 3/1994 | Egusa et al. |
| 5,545,639 | A | 8/1996 | Rabinovitz et al. |
| 6,004,709 | A | 12/1999 | Renfer et al. |
| 6,232,714 | B1 | 5/2001 | Shen et al. |
| 6,307,528 | B1 | 10/2001 | Yap |
| 6,310,360 | B1 | 10/2001 | Forrest et al. |
| 6,344,505 | B1 | 2/2002 | Valentine, Jr. et al. |
| 6,716,371 | B1 | 4/2004 | Sage et al. |
| 6,723,445 | B2 | 4/2004 | Li et al. |
| 6,740,407 | B1 | 5/2004 | Usuki et al. |
| 7,265,378 | B2 | 9/2007 | Lecloux et al. |
| 2002/0045061 | A1 | 4/2002 | Hosokawa |
| 2002/0055015 | A1 | 5/2002 | Sato |
| 2002/0135292 | A1 | 9/2002 | Kamatani et al. |
| 2003/0169554 | A1* | 9/2003 | Nakagawa et al. ........ 361/301.1 |
| 2003/0197158 | A1 | 10/2003 | Lee et al. |
| 2004/0077860 | A1 | 4/2004 | Herron et al. |

FOREIGN PATENT DOCUMENTS

| | | |
|---|---|---|
| EP | 1013740 A2 | 6/2000 |
| EP | 1097981 A2 | 5/2001 |
| EP | 1182183 A1 | 2/2002 |
| EP | 1215945 A2 | 6/2002 |
| FR | 2099783 A5 | 3/1972 |
| GB | 1047796 A | 11/1966 |
| JP | 50108014 A | 8/1975 |
| JP | 55017105 A | 2/1980 |
| JP | 55098754 A | 7/1980 |
| JP | 60106858 A | 6/1985 |
| JP | 61041152 A | 2/1986 |
| JP | 61051151 A | 3/1986 |
| JP | 62174981 A | 7/1987 |
| JP | 01103484 A | 4/1989 |
| JP | 01208873 A | 8/1989 |
| JP | 02064553 A | 3/1990 |
| JP | 04110390 A | 4/1992 |
| JP | 05247357 A | 9/1993 |
| JP | 06088072 A | 3/1994 |
| JP | 07026255 A | 1/1995 |
| JP | 07152170 A | 6/1995 |
| JP | 09188874 A * | 7/1997 |
| JP | 2000046949 A | 2/2000 |
| JP | 2000133453 A | 5/2000 |
| JP | 2000198788 A | 7/2000 |
| JP | 2000204082 A | 7/2000 |
| JP | 2001110572 A | 4/2001 |
| JP | 2001267080 A | 9/2001 |
| JP | 2001335776 A | 12/2001 |
| JP | 2002352961 A | 12/2002 |
| JP | 2003045662 A | 2/2003 |
| JP | 2003086381 A | 3/2003 |
| WO | 9948160 A1 | 9/1999 |
| WO | 0070655 A2 | 11/2000 |
| WO | 0172925 A1 | 10/2001 |
| WO | 0230159 A1 | 4/2002 |
| WO | 0243449 A1 | 5/2002 |
| WO | 0251206 A2 | 6/2002 |
| WO | 02088274 A1 | 11/2002 |
| WO | 02091814 A2 | 11/2002 |
| WO | 02101838 A1 | 12/2002 |
| WO | 03079737 A2 | 9/2003 |

OTHER PUBLICATIONS

Adachi et al., "Nearly 100% Internal Phosphorescence Efficiency in an Organic Light Emitting Device," Journal of Applied Physics, 2001, vol. 90, pp. 5048-5051.
Beilstein Record No. 8797439 2006.
Borsenberger et al., "Hole Transport in Triphenylmethane-doped Poly(styrene)," Journal of Imaging Science and Technology, 1997, vol. 41, No. 2, pp. 185-191.
Borsenberger et al., "Hole Transport in Vapor-Deposited Triphenylmethane Glasses," Japanese Journal of Applied Physics, 1996, vol. 35, Pt. 1, No. 5A, pp. 2698-2703.
Borsenberger et al., "Effects of the Dipole Moment on Charge Transport in Disordered Molecular Solids," The Journal of Physical Chemistry, 1993, vol. 97(18), pp. 4815-4819.
Chao et al, "Effect of Side Chain Alkyl Length on the Electroluminescence Characteristics fo Carbazole-Based Light Emitting Polymers," Macromol, Chem Phys., 2001, vol. 202, pp. 2864-2871.
Cui et al., "Thiophene-Linked Polyphenylquinoxaline: A New Electron Transport Conjugated Polymer for Electroluminescent Devices," Macromolecules, 1999, vol. 32, pp. 3824-3826.
Dietrich-Buchecker et al., "Selective and efficient synthesis of di-, tri- and tetrasubstituted 1,10-phenanthrolines," Tetrahedron Letters, 1999, vol. 40, pp. 3395-3396.
Filler et al, "Fluorocarbon Chemistry-Tris(4-nitro-2,3,5,6-tetra flourophenyl)methane and companions," Journal of Fluorine Chemistry, 2000, vol. 102, pp. 185-188.
Gibson et al., "Surface Analyses by a Triboelectric Charging Techniques," Analytical Chemistry, 1979, vol. 51, No. 4, pp. 483-487.
Giebeler et al., "The photovoltaic effect in poly(p-phenylene-2,3'-bis(3,2'-diphenyl)-quinoxaline-7-7'-diyl)," Optical Materials, 1998, vol. 9, pp. 99-103.
Gruenbaum et al., "Hole Transport in Triphenylmethane Doped Polymers," Japanese Journal of Appllied Physics, 1996, vol. 35, Pt. 1, No. 5A, pp. 2704-2708.
Hallas et al, "Dyes Containing Flourine-I; Electronic Absorbtion Spectrum of 2,3,4,5,6-Pentaflouro Malachite Green and the Effect of the Pentaflourophenyl Group," Tetrahedron, 1972, vol. 28, pp. 893-896.
Jandke et al., "Phenylquinoxaline Polymers and Low Molar Mass Glasses as Electron-Transport Materials in Organic Light-Emitting Diodes," Macromolecules, 1998, vol. 31, pp. 6434-6443.
Jin et al., "Blue electroluminescence in blend of polymers containing carbazole and 1,3,4-oxadiazole units," Thin Solid Films, 2000, vol. 363, pp. 255-258.
Kuder et al., "Anodic and Photochemical Oxidation of Triphenylmethanes," J. Org. Chem., 1979, vol. 44, pp. 761-766.
Limburg et al., "Electronic Transport Properties of Molecularly Doped Polymers—Some Substituted Triarylmethanes, Organic Coatings and Plastics," Chemistry, 1978, vol. 38, pp. 534-539.
Malpert et al., "Color intensity control in polymers using triarylmethane leuconitriles as color formers," Tetrahedron, 2001, vol. 57, pp. 967-974.
Naka et al., "High electron mobility in bathophenanthroline," Applied Physics Letters, 2000, vol. 76(2), pp. 197-199.
Nguyen et al., "Multilayer light emitting diodes using a PPV based copolymer," Optical Materials, 1998, vol. 9, pp. 154-158.
O'Brien et al., "Use of poly(phenyl quinoxaline) as an electron transport material in polymer light-emitting diodes," Applied Physics Letters, 1996, vol. 69(7), pp. 881-883.
Posch et al., "Perylenediimides with Electron Transport Moieties for Electroluminescent Devices," Synthetic Materials, 1999, vol. 102, pp. 1110-1112.
Redecker et al., "Electron transport in starburst phenylquinoxalines," Applied Physics Letter, 1999, vol. 75(1), pp. 109-111.
Rehahn et al, "Synthesis, solution properties and conversion of poly(2,9-o-phenanthroline-alt-(2',5'-dihexyl)-4,4"-p-terphenylene)s into soluble, well-defined copper(I) and silver (I) complex polymers," Macromol. Chem. Phys., 1998, vol. 199, pp. 127-140.
Schmitz et al., "Polymeric Light-Emitting Diodes Based on Poly(p-phenylene ethynylene), Poly(triphenyldiamine), and Spiroquinoxaline," Advanced Functional Materials, 2001, vol. 11(1), pp. 41-46.
Schurmann et al., "Ultraviolet Photoelectron Spectroscopic Study of Heterocyclic Model Compounds for Electroluminescent Devices," Synthetic Metals, 1999, vol. 102, pp. 1069-1070.
Sun et al., "PVC membrane lithium-selective electrodes based on oligomethylene-bridged bis-1,10-phenanthroline derivatives," Analytica Chimica Acta, 1996, vol. 329, pp. 57-64.

Suzuki et al, "A New Stereospecific Cross-Coupling by the Palladium-Catalyzed Reaction of 1-Alkenylboranes with 1-Alkenyl or 1-Alkynyl Halides," Tetrahedron Letters, 1979, No. 36, pp. 3437-3440.

Thomas et al., "Quinoxalines Incorporating Triarylamines: Potential Electroluminescent Materials with Tunable Emission Characteristics," Chem. Mater., 2002, vol. 14, pp. 2796-2802.

Yamamoto et al, "Electrically conducting and thermally stable ☐-conjugated poly(arylene)s prepared by organometallic process," Progress in Polymer Science, 1992, vol. 17, pp. 1153-1205.

Yamamoto et al., "Preparation and Properties of ☐-Conjugated Poly(1,10-phenanthroline03,8-diyl)," Chemistry Letters, 1995, pp. 785-786.

Yamamoto et al., "Preparation of New Electron-Accepting p-conjugated Polyquinoxalines. Chemical and Electrochemical Reduction, Electrically Conducting Properties, and Use in Light-Emitting Diodes," J. Am. Chem. Soc., 1996, vol. 118, pp. 3930-3937.

Young et al., "Dipole Moments of Hole-Transporting Materials and Their Influence on Hole Mobility in Molecularly Doped Polymers," J. Phys. Chem., 1995, vol. 99(12), pp. 4230-4240.

Zhao et al, "Photorefractive Polymer with Side-Chain Second Order Nonlinear Optica and Charge-Transporting Groups," Chem. Mater., 1995, vol. 7, pp. 1237-1242.

Zhu et al., "A relationship between driving voltage and the highest occupied molecular orbital level of hole-transporting metallophthalocyanine layer for organic electroluminescence devices," Thin Solid Films, 2001, vol. 396, pp. 213-218.

Zotti et al., "Electrochemical, Conductive, and Magnetic Properties of 2,7-Carbazole-Based Conjugated Polymers," Macromolecules, 2002, vol. 35, pp. 2122-2128.

PCT International Search Report for International Application No. PCT/US 03/021610, M. Fritz Authorized Officer, Apr. 6, 2004.

PCT International Search Report for International Application No. PCT/US 03/021612, N. Doslik Authorized Officer, Mar. 15, 2004.

PCT International Search Report for International Application No. PCT/US 03/021613, D. Marsitzky Authorized Officer, Feb. 26, 2004.

PCT International Search Report for International Application No. PCT/US 03/021617, C. Pusch Authorized Officer, Feb. 24, 2004.

PCT International Search Report for International Application No. PCT/US 03/021618, S. Fanni Authorized Officer, Jan. 28, 2004.

\* cited by examiner (I)

(II)

(III)

I(a)

I(b)

I(c)

I(d)

I(e)

I(f)

I(g)

I(h)

I(i)

I(j)

I(k)

I(l)

I(m)

I(n)

I(o)

I(p)

I(q)

I(r)

I(s)

I(t)

I(u)

I(v)

I(w)

I(x)

I(y)

I(z)

I(aa)

I(ab)

I(ac)

I(ad)

I(ae)

I(af)

I(ag)

IV(a)

IV(b)

IV(c)

IV(d)

IV(e)

IV(f)

IV(g)

IV(h)

II(a)

II(b)

II(c)

II(d)

II(j)

II(k)

II(l)

II(m)

V(a)

V(b)

V(c)

V(d)

V(e)

DDPA (Compound F)

DPA (Compound G)

CHARGE TRANSPORT COMPOSITIONS AND ELECTRONIC DEVICES MADE WITH SUCH COMPOSITIONS

CROSS REFERENCE TO RELATED APPLICATIONS

This application is a division of U.S. application Ser. No. 13/029,458, filed on Feb. 17, 2011, which in turn was a division of U.S. application Ser. No. 12/126,061 filed May 23, 2008, now allowed, which is a division of 10/612,704, filed Jul. 10, 2003, now U.S. Pat. No. 7,399,432, which claims priority from U.S. Provisional Application Ser. No. 60/394,767, filed Jul. 10, 2002, and U.S. Provisional Application Ser. No. 60/458,277, filed Mar. 28, 2003, both of which are incorporated by reference herein in their entirety.

BACKGROUND OF THE INVENTION

1. Field of the Invention

The present invention relates to charge transport compositions. The invention further relates to photoactive electronic devices in which there is at least one active layer comprising such charge transport compositions.

2. Background

In organic photoactive electronic devices, such as light-emitting diodes ("OLED"), that make up OLED displays, the organic active layer is sandwiched between two electrical contact layers in an OLED display. In an OLED the organic photoactive layer emits light through the light-transmitting electrical contact layer upon application of a voltage across the electrical contact layers.

It is well known to use organic electroluminescent compounds as the active component in light-emitting diodes. Simple organic molecules, conjugated polymers, and organometallic complexes have been used.

Devices which use photoactive materials, frequently include one or more charge transport layers, which are positioned between the photoactive (e.g., light-emitting layer) layer and one of the contact layers. A hole transport layer may be positioned between the photoactive layer and the hole-injecting contact layer, also called the anode. An electron transport layer may be positioned between the photoactive layer, such as the organometallic light emitting material, in photoactive devices, and the electron-injecting contact layer, also called the cathode.

There is a continuing need for charge transport materials and anti-quenching materials.

SUMMARY OF THE INVENTION

The present invention is directed to a charge transport composition which is a quinoxaline derivative. The quinoxaline derivative has Formula I, shown in FIG. 1, wherein:

$R^1$ and $R^2$ are the same or different at each occurrence and are selected from H, F, Cl, Br, hydroxyl, carboxyl, carbonyl, silyl, siloxyl, alkyl, heteroalkyl, alkenyl, alkynyl, aryl, heteroaryl, alkylenearyl, alkenylaryl, alkynylaryl, alkyleneheteroaryl, alkenylheteroaryl, alkynylheteroaryl, $C_nH_aF_b$, $OC_nH_aF_b$, $C_6H_cF_d$, and $OC_6H_cF_d$, or both of $R^2$ together may constitute an arylene or heteroarylene group;

a, b, c, and d are 0 or an integer such that $a+b=2n+1$, and $c+d=5$, n is an integer from 1 through 12; and z is 0 or an integer from 1 through 4.

In another embodiment, the present invention is directed to a charge transport composition having Formula II, shown in FIG. 2, wherein:

$R^1$, $R^2$, a through d and n are as defined above, $R^3$ is the same or different at each occurrence and is selected from a single bond and a group selected from alkylene, heteroalkylene, arylene, heteroarylene, arylenealkylene, and heteroarylenealkylene; alkynylene, alkynylenearylene, alkynyleneheteroarylene.

Q is selected from a single bond and a multivalent group;

m is an integer equal to at least 2, p is 0 or 1 and x is 0 or an integer from 1 to 3.

In another embodiment, the present invention is directed to a charge transport composition having Formula III, shown in FIG. 3, wherein:

$R^1$, $R^2$, a through d, n, and z are as defined above, $R^3$ is the same or different at each occurrence and is selected from a single bond and a group selected from alkylene, heteroalkylene, arylene, heteroarylene, arylenealkylene, and heteroarylenealkylene; alkynylene, alkynylenearylene, alkynyleneheteroarylene.

Q is selected from a single bond and a multivalent group;

m is an integer equal to at least 2; and p is 0 or 1.

In another embodiment, the present invention is directed to an electronic device having at least one active layer comprising a material selected from Formulae I, II, and III, shown in FIGS. 1 through 3, wherein $Ar^1$, $R^1$ through $R^3$, Q, a through d, m, n, p, x, and z are as defined above.

As used herein, the term "charge transport composition" is intended to mean material that can receive a charge from an electrode and facilitates movement through the thickness of the material with relatively high efficiency and small loss of charge. Hole transport compositions are capable of receiving a positive charge from an anode and transporting it. Electron transport compositions are capable of receiving a negative charge from a cathode and transporting it. The term "anti-quenching composition" is intended to mean a material which prevents, retards, or diminishes both the transfer of energy and the transfer of an electron to or from the excited state of the photoactive layer to an adjacent layer. The term "photoactive" refers to any material that exhibits electroluminescence, photoluminescence, and/or photosensitivity. The term "HOMO" refers to the highest occupied molecular orbital of a compound. The term "LUMO" refers to the lowest unoccupied molecular orbital of a compound. The term "group" is intended to mean a part of a compound, such as a substituent in an organic compound. The prefix "hetero" indicates that one or more carbon atoms has been replaced with a different atom. The term "alkyl" is intended to mean a group derived from an aliphatic hydrocarbon having one point of attachment, which group may be unsubstituted or substituted. The term "heteroalkyl" is intended to mean a group derived from an aliphatic hydrocarbon having at least one heteroatom and having one point of attachment, which group may be unsubstituted or substituted. The term "alkylene" is intended to mean a group derived from an aliphatic hydrocarbon and having two or more points of attachment. The term "heteroalkylene" is intended to mean a group derived from an aliphatic hydrocarbon having at least one heteroatom and having two or more points of attachment. The term "alkenyl" is intended to mean a group derived from a hydrocarbon having one or more carbon-carbon double bonds and having one point of attachment, which group may be unsubstituted or substituted. The term "alkynyl" is intended to mean a group derived from a hydrocarbon having one or more carbon-carbon triple bonds and having one point of attachment, which group may be unsubstituted or substituted. The term "alkenylene" is intended to mean a group derived from a hydrocarbon having one or more carbon-carbon double bonds and having two or more points of attachment, which group may be unsubstituted or substituted. The term "alkynylene" is intended to mean a group derived from a hydrocarbon having one or more carbon-carbon triple bonds and having two or more points of attachment, which group may be unsubstituted or substituted. The terms "heteroalkenyl", "heteroalkenylene", "heteroalkynyl" and "heteroalkynlene" are intended to mean analogous groups having one or more heteroatoms. The term "aryl" is intended to mean a group derived from an aromatic hydrocarbon having one point of attachment, which group may be unsubstituted or substituted. The term "heteroaryl" is intended to mean a group derived from an aromatic group having at least one heteroatom and having one point of attachment, which group may be unsubstituted or substituted. The term "arylalkylene" is intended to mean a group derived from an alkyl group having an aryl substituent, which group may be further unsubstituted or substituted. The term "heteroarylalkylene" is intended to mean a group derived from an alkyl group having a heteroaryl substituent, which group may be further unsubstituted or substituted. The term "arylene" is intended to mean a group derived from an aromatic hydrocarbon having two points of attachment, which group may be unsubstituted or substituted. The term "heteroarylene" is intended to mean a group derived from an aromatic group having at least one heteroatom and having two points of attachment, which group may be unsubstituted or substituted. The term "arylenealkylene" is intended to mean a group having both aryl and alkyl groups and having one point of attachment on an aryl group and one point of attachment on an alkyl group. The term "heteroarylenealkylene" is intended to mean a group having both aryl and alkyl groups and having one point of attachment on an aryl group and one point of attachment on an alkyl group, and in which there is at least one heteroatom. Unless otherwise indicated, all groups can be unsubstituted or substituted. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "compound" is intended to mean an electrically uncharged substance made up of molecules that further consist of atoms, wherein the atoms cannot be separated by physical means. The term "ligand" is intended to mean a molecule, ion, or atom that is attached to the coordination sphere of a metallic ion. The term "complex", when used as a noun, is intended to mean a compound having at least one metallic ion and at least one ligand. The term "polymeric" is intended to encompass oligomeric species and include materials having 2 or more monomeric units. In addition, the IUPAC numbering system is used throughout, where the groups from the Periodic Table are numbered from left to right as 1 through 18 (CRC Handbook of Chemistry and Physics, 81$^{st}$ Edition, 2000).

Unless otherwise defined, all technical and scientific terms used herein have the same meaning as commonly understood by one of ordinary skill in the art to which this invention belongs. Unless otherwise defined, all letter symbols in the figures represent atoms with that atomic abbreviation. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE PREFERRED EMBODIMENTS

Figure 1:
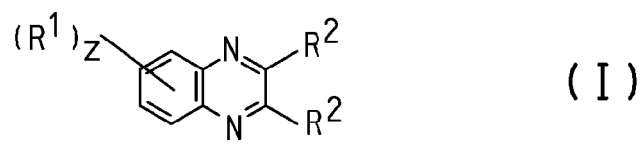
FIG. 1 shows Formula I for a charge transport composition of the invention.

The quinoxaline derivative compounds represented by Formula I, shown in FIG. 1, have particular utility as electron transport compositions and as anti-quenching agents. The quinoxaline compounds can also be used as hosts for light emitting materials.

In general, n is an integer. In one embodiment, n is an integer from 1 through 20. In one embodiment, n is an integer from 1 through 12.

In one embodiment, $R^1$ is selected from phenylalkenyl and phenylakynyl groups, which may be further substituted.

In one embodiment, $R^1$ is selected from alkylacetate and arylcarbonyl groups, which may be further substituted.

In one embodiment, $R^1$ is selected from alkyl groups having 1 through 12 carbon atoms.

In one embodiment, $R^2$ is selected from phenyl groups, substituted phenyl groups, pyridyl groups, and substituted pyridyl groups. The substituent can be selected from F, Cl, Br, hydroxyl, carboxyl, carbonyl, silyl, siloxyl, alkyl, heteroalkyl, alkenyl, alkynyl, aryl, heteroaryl, alkylenearyl, alkenylaryl, alkynylaryl, alkyleneheteroaryl, alkenylheteroaryl, alkynylheteroaryl, $C_nH_aF_b$, $OC_nH_aF_b$, $C_6H_cF_d$, and $OC_6H_cF_d$.

In one embodiment, both of $R^2$ together are a biarylene group, which may be further substituted. In one embodiment, the biarylene group is selected from biphenylene and bipyridylene. The substituent can be selected from F, Cl, Br, hydroxyl, carboxyl, cabonyl, silyl, siloxyl, alkyl, heteroalkyl, alkenyl, alkynyl, aryl, heteroaryl, alkylenearyl, alkenylaryl, alkynylaryl, alkyleneheteroaryl, alkenylheteroaryl, alkynylheteroaryl, $C_nH_aF_b$, $OC_nH_aF_b$, $C_6H_cF_d$, and $OC_6H_cF_d$.

Examples of suitable ET/AQ compounds of this type include, but are not limited to those given as Formulae I(a) through I(ag) in FIG. 4.

The compositions represented by Formula I can be prepared using standard synthetic organic techniques, as illustrated in the examples. The compounds can be applied as thin films by evaporative techniques or conventional solution processing methods. As used herein, "solution processing" refers to the formation of films from a liquid medium. The liquid medium can be in the form of a solution, a dispersion, an emulsion, or other forms. Typical solution processing techniques include, for example, solution casting, drop casting, curtain casting, spin-coating, screen printing, inkjet printing, gravure printing, and the like.

Figure 2:
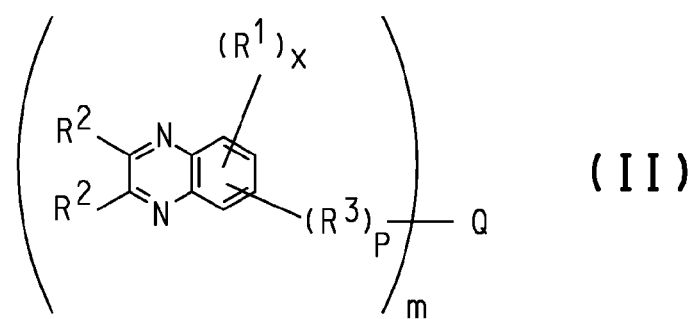
FIG. 2 shows Formula II for a charge transport composition of the invention.
Figure 3:
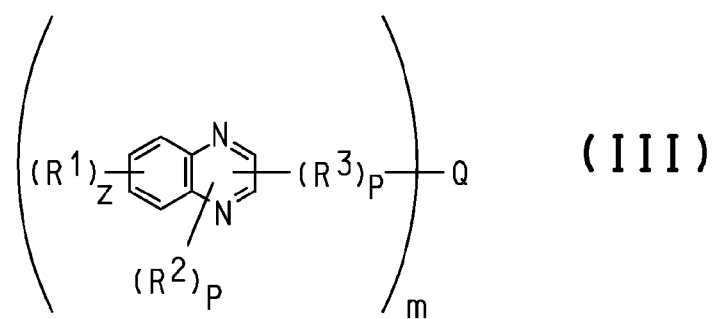
FIG. 3 shows Formula III for a charge transport composition of the invention.
Figure 4A:
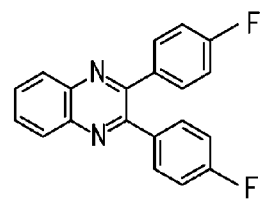
FIG. 4 shows Formulae I(a) through I(ag) for a charge transport composition of the invention.
Figure 4B:
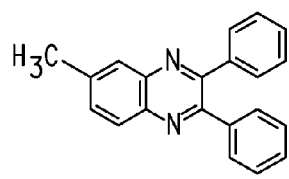
Figure 4C:
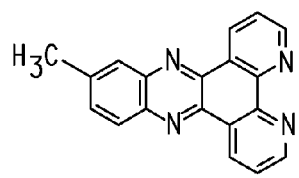
Figure 4D:
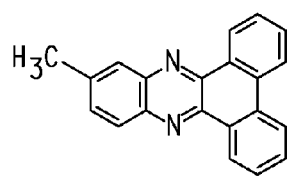
Figure 4E:
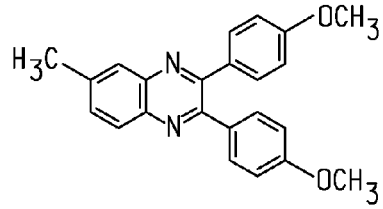
Figure 4F:
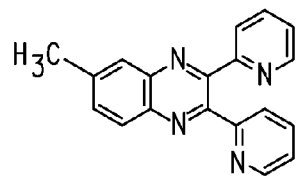
Figure 4G:
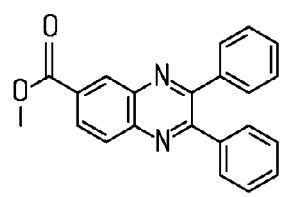
Figure 4H:
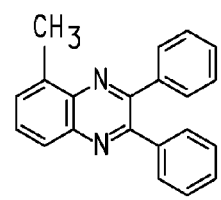
Figure 4I:
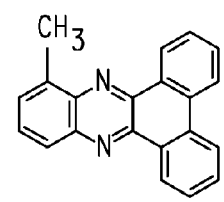
Figure 4J:
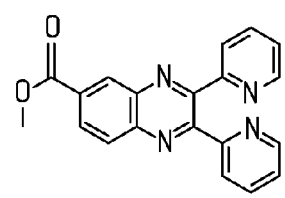
Figure 4K:
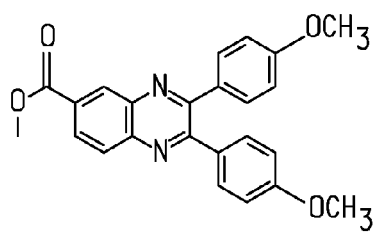
Figure 4L:
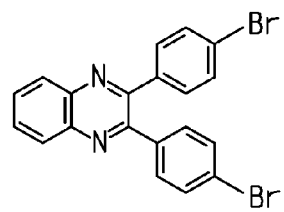
Figure 4M:
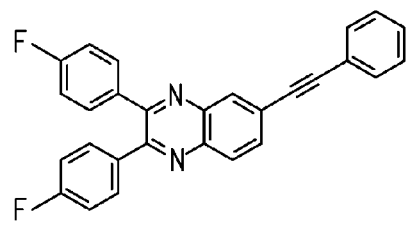
Figure 4N:
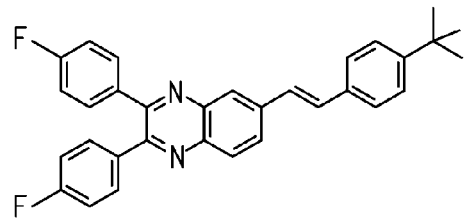
Figure 4O:
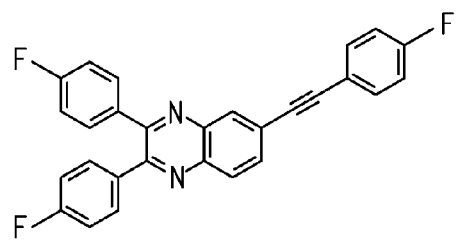
Figure 4P:
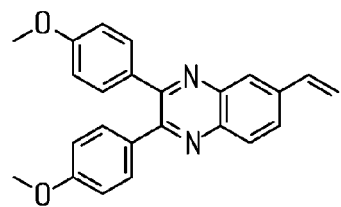
Figure 4Q:
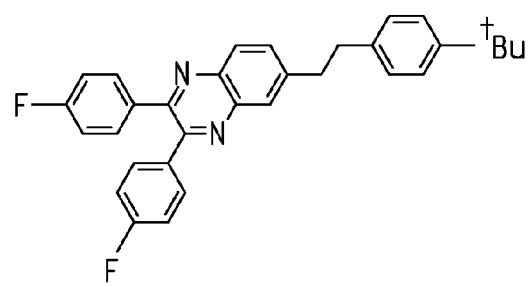
Figure 4R:
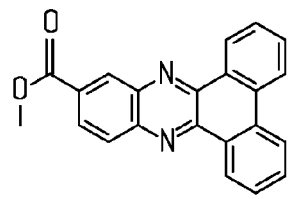
Figure 4S:
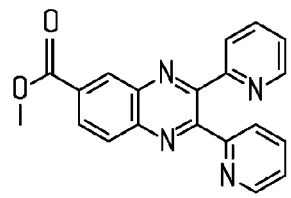
Figure 4T:
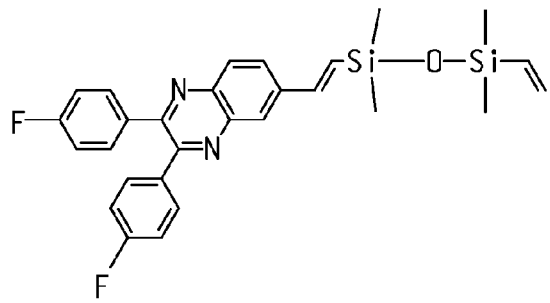
Figure 4U:
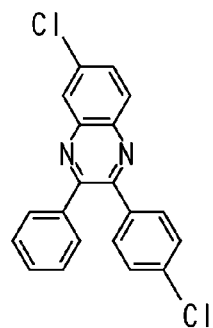
Figure 4V:
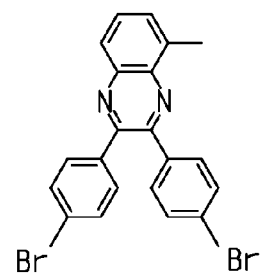
Figure 4W:
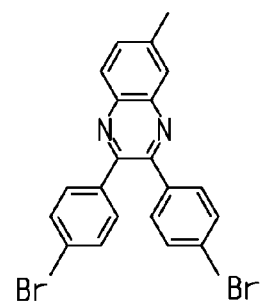
Figure 4X:
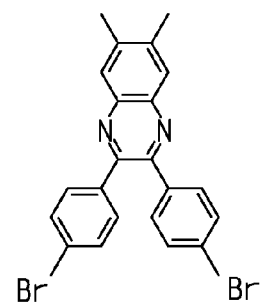
Figure 4Y:
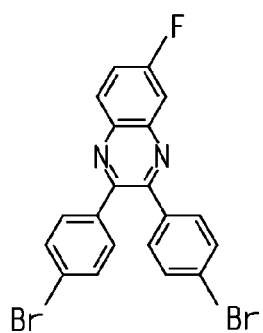
Figure 4Z:
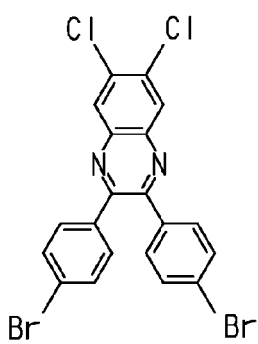
Figure 4A:
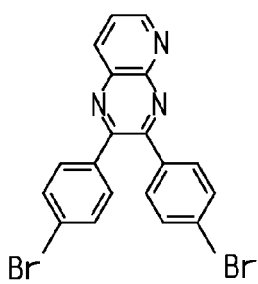
Figure 4A:
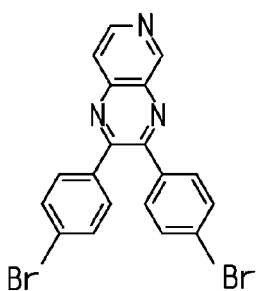
Figure 4A:
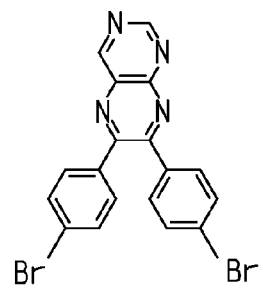
Figure 4A:
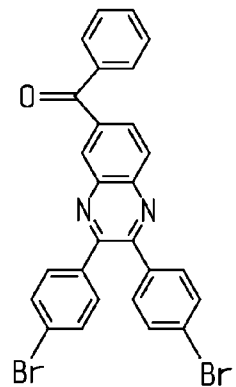
Figure 4A:
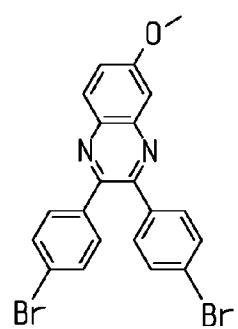
Figure 4A:
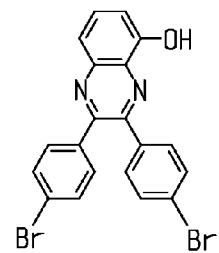
Figure 4A:
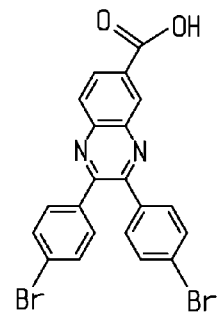
Figure 5A:
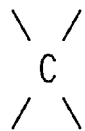
FIG. 5 shows Formulae IV(a) through IV(h) for a multidentate linking group.
Figure 5B:
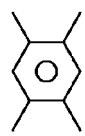
Figure 5C:
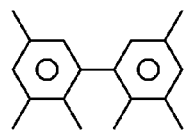
Figure 5D:
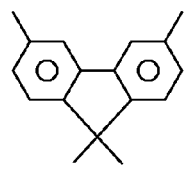
Figure 5E:
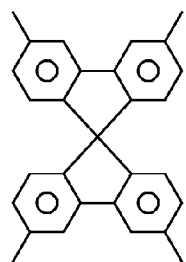
Figure 5F:
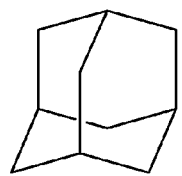
Figure 5G:
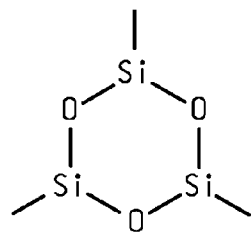
Figure 5H:
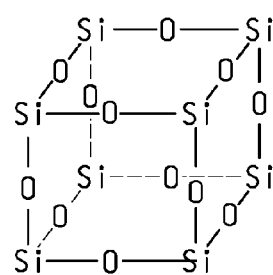
Figure 6A:
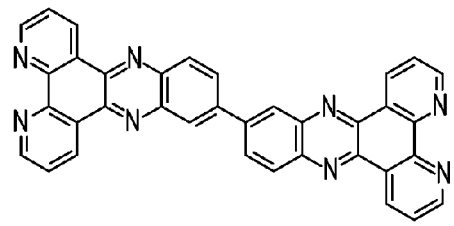
FIG. 6 shows Formulae II(a) through II(l) for a charge transport composition of the invention.
Figure 6B:
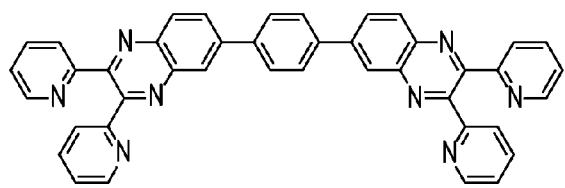
Figure 6C:
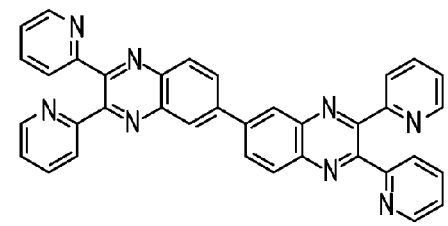
Figure 6D:
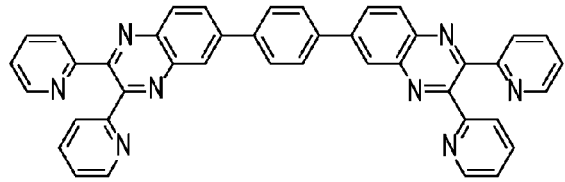
Figure 6E:
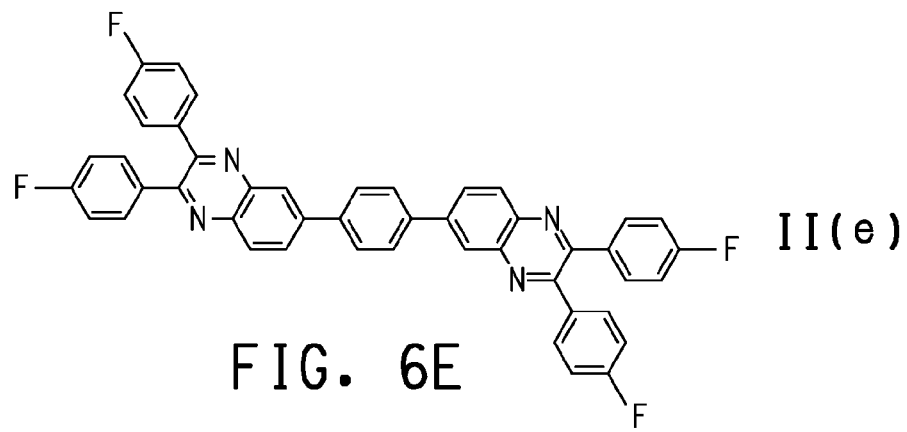
Figure 6F:
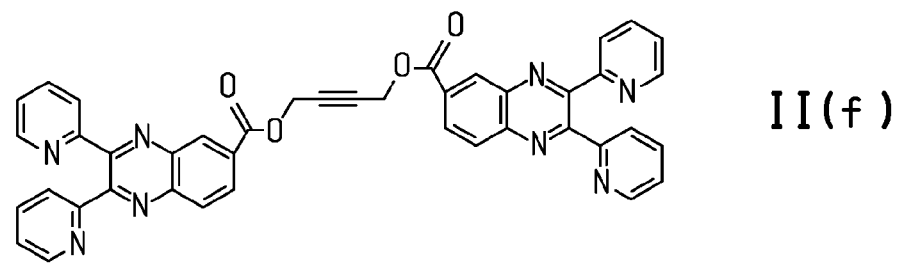
Figure 6G:
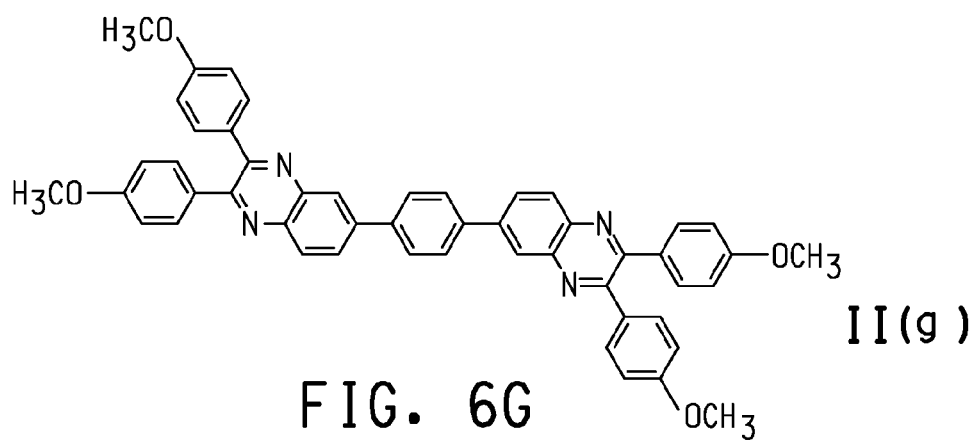
Figure 6H:
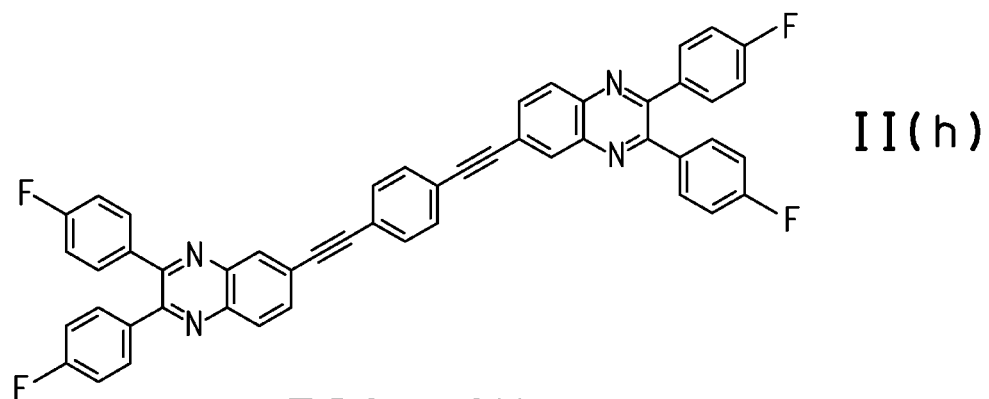
Figure 6I:
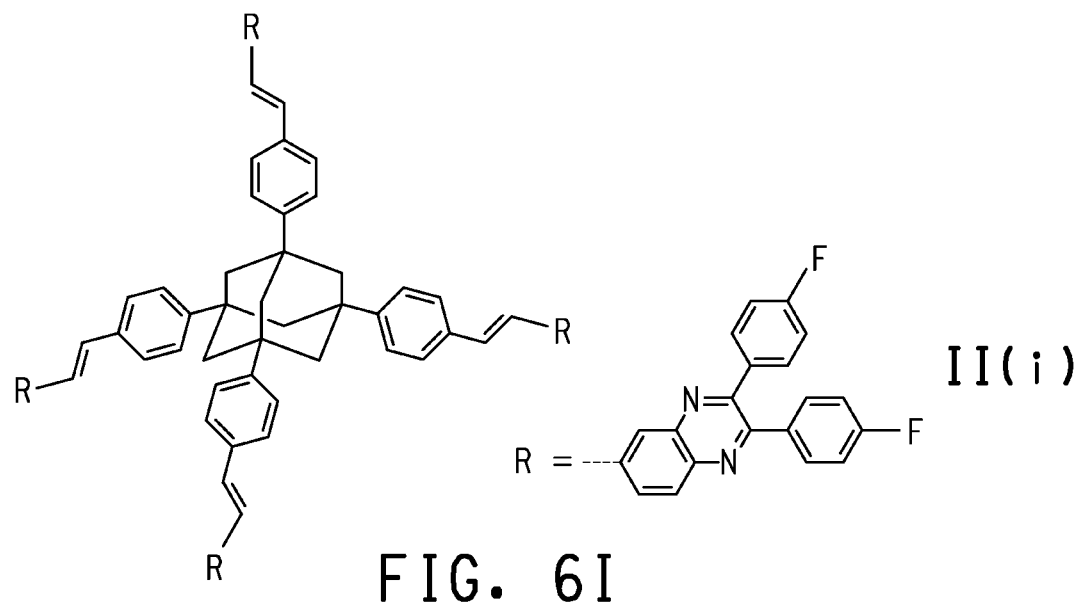
Figure 6J:
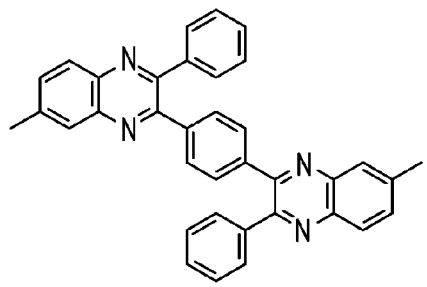
Figure 6K:
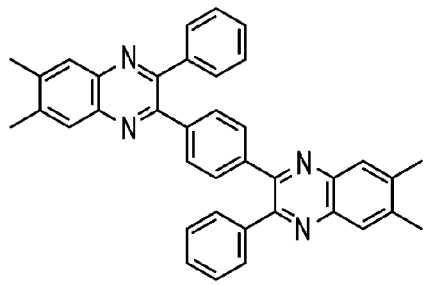
Figure 6L:
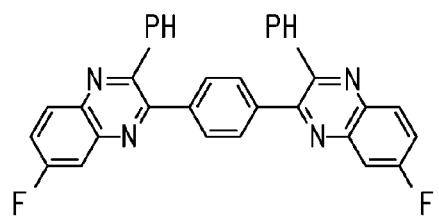
Figure 6M:
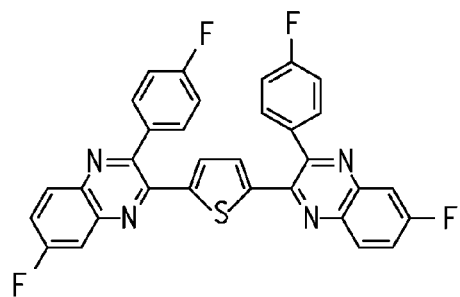
Figure 7A:
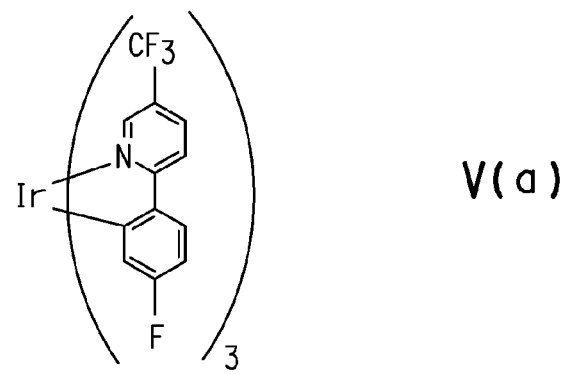
FIG. 7 shows Formulae V(a) through V(e) for electroluminescent iridium complexes.
Figure 7B:
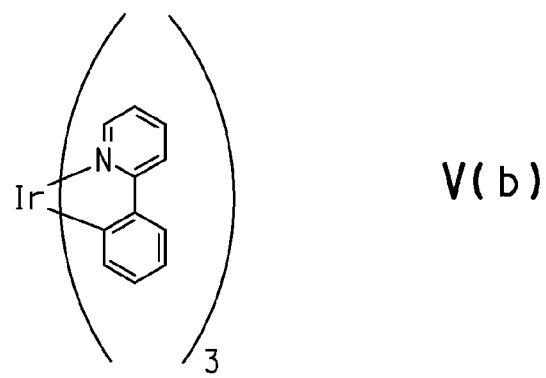
Figure 7C:
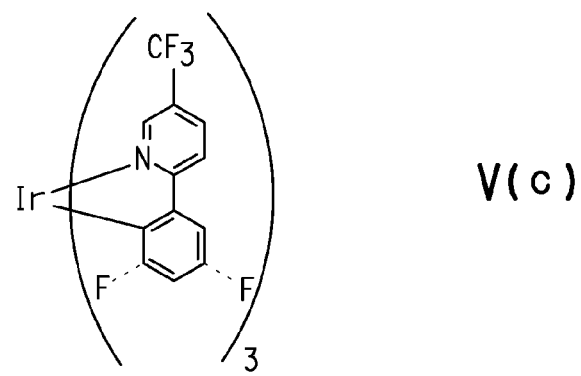
Figure 7D:
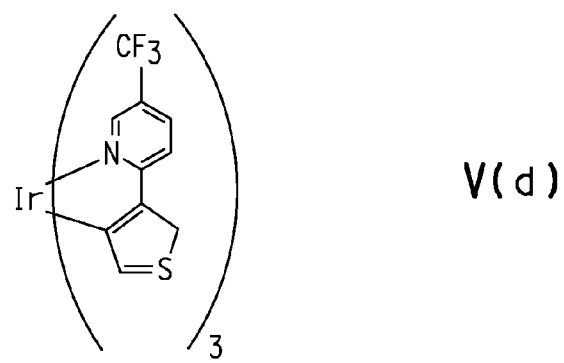
Figure 7E:
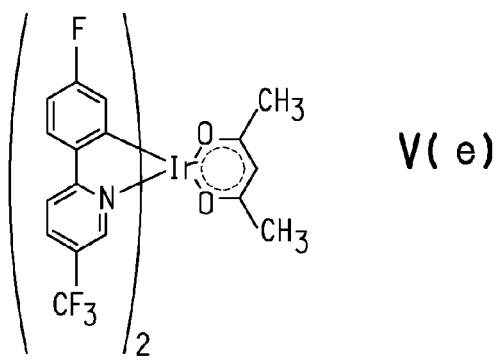

In some cases it is desirable to increase the Tg of the compounds to improve stability, coatability, and other properties. This can be accomplished by linking together two or more of the compounds with a linking group to form compounds having Formula II, shown in FIG. 2, or Formula III, shown in FIG. 3. In these formulae, Q can be a single bond or a multivalent linking group, having two or more points of attachment. The multivalent linking group can be a hydrocarbon group with two or more points of attachment, and can be aliphatic or aromatic. The multivalent linking group can be a heteroalkylene or heteroarylene group, where the heteroatoms can be, for example, N, O, S, or Si. Examples of multivalent groups, Q, include, but are not limited to, alkylene, alkenylene, and alkynylene groups, and analogous compounds with heteroatoms; single, multiple-ring, and fused-ring aromatics and heteroaromatics; arylamines, such as triarylamines; silanes and siloxanes. Additional examples of multivalent Q groups are given in FIG. 5 as Formulae IV(a) through IV(h). In Formula IV(f), any of the carbons may be linked to a charge transport moiety. In Formula IV(h), any of the Si atoms can be linked to a charge transport moiety. Heteroatoms such as Ge and Sn can also be used. The linking group can also be —[SiMeR$^1$—SiMeR$^1$]$_n$—, where R$^1$ and n are as defined above.

In general, m is an integer equal to at least 2. The exact number depends on the number of available linking positions on Q and on the geometries of the quinoxaline moiety and Q. In one embodiment, m is an integer from 2 through 10.

In one embodiment, in Formula II, R$^1$ is selected from phenyl and substituted phenyl groups. The substituents can be selected from F, Cl, Br, alkyl, heteroalkyl, alkenyl, and alkynyl.

In one embodiment, in Formula II, R$^1$ is selected from alkylacetate and arylcarbonyl groups, which may be further substituted.

In one embodiment, in Formula II, R$^1$ is selected from alkyl groups having 1 through 12 carbon atoms.

In one embodiment, in Formula II, R$^2$ is selected from phenyl groups, substituted phenyl groups, pyridyl groups, and substituted pyridyl groups. The substituent can be selected from F, Cl, Br, hydroxyl, carboxyl, carbonyl, silyl, siloxyl, alkyl, heteroalkyl, alkenyl, alkynyl, aryl, heteroaryl, alkylenearyl, alkenylaryl, alkynylaryl, alkyleneheteroaryl, alkenylheteroaryl, alkynylheteroaryl, C$_n$H$_a$F$_b$, OC$_n$H$_a$F$_b$, C$_6$H$_c$F$_d$, and OC$_6$H$_c$F$_d$.

In one embodiment, in Formula II, both of R$^2$ together are a biarylene group, which may be further substituted. In one embodiment, the biarylene group is selected from biphenylene and bipyridylene. The substituent can be selected from F, Cl, Br, hydroxyl, carboxyl, cabonyl, silyl, siloxyl, alkyl, heteroalkyl, alkenyl, alkynyl, aryl, heteroaryl, alkylenearyl, alkenylaryl, alkynylaryl, alkyleneheteroaryl, alkenylheteroaryl, alkynylheteroaryl, C$_n$H$_a$F$_b$, OC$_n$H$_a$F$_b$, C$_6$H$_c$F$_d$, and OC$_6$H$_c$F$_d$.

In one embodiment, in Formula II, x is 0.

In one embodiment, in Formula II, R$^3$ is selected from aryl, heteroaryl, alkyl, and heteroalkyl. In one embodiment, in Formula II, R$^3$ is selected from phenyl and substituted phenyl. In one embodiment, in Formula II, R$^3$ is selected from alkyl and heteroalkyl having from 1 through 12 carbon atoms, which may be further substituted.

In one embodiment, in Formula III, R$^1$ is selected from phenylalkenyl and phenylakynyl groups, which may be further substituted.

In one embodiment, in Formula III, R$^1$ is selected from alkylacetate and arylcarbonyl groups, which may be further substituted.

In one embodiment, in Formula III, R$^1$ is selected from alkyl groups having 1 through 12 carbon atoms.

In one embodiment in Formula III, R$^2$ is H.

In one embodiment in Formula III, R$^3$ is selected from aryl, heteroaryl, alkyl, and heteroalkyl. In one embodiment, in Formula III, R$^3$ is selected from phenyl and substituted phenyl. In one embodiment, in Formula III, R$^3$ is selected from alkyl and heteroalkyl having from 1 through 12 carbon atoms, which may be further substituted.

Specific examples of linked compounds having Formula II are given in FIG. 6, Formulae II(a) through II(l).

Electronic Device

Figure 8:
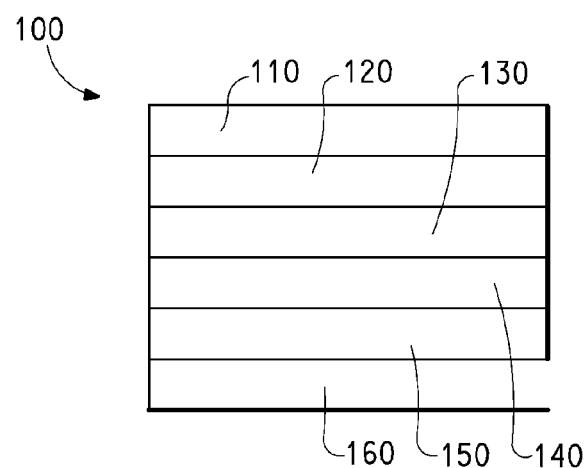
FIG. 8 is a schematic diagram of a light-emitting diode (LED).

The present invention also relates to an electronic device comprising at least one of the charge transport compositions of the invention positioned between a photoactive layer and one electrode. A typical device structure is shown in FIG. 8. The device 100 has an anode layer 110 and a cathode layer 160. Adjacent to the anode is a layer 120 comprising hole transport material. Adjacent to the cathode is a layer 140 comprising an electron transport and/or anti-quenching material ("ET/AQ"). Between the hole transport layer and the electron transport and/or anti-quenching layer is the photoactive layer 130. As an option, devices frequently use another electron transport layer 150, next to the cathode. Layers 120, 130, 140, and 150 are individually and collectively referred to as the active layers.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are describe in Markus, John, *Electronics and Nucleonics Dictionary*, 470 and 476 (McGraw-Hill, Inc. 1966).

The quinoxaline derivative compounds of the invention are particularly useful as the electron transport and/or anti-quenching composition in layer 140, or as electron transport composition in layer 150. For example, in one embodiment, the quinoxaline derivative compounds of the invention may be used as the electron transport and/or anti-quenching layer in light emitting diode.

It is also to be understood that the ET/AQ material has to be chemically compatible with the photoactive material used. For example, the ET/AQ material has to form a smooth film when deposited on the photoactive material layer. If aggregation occurs, the performance of the device will deteriorate.

The other layers in the device can be made of any materials which are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode 110 may also comprise an organic material such as polyaniline as described in "Flexible light-emitting diodes made from soluble conducting polymer," Nature vol. 357, pp 477-479 (11 Jun. 1992). At least one of the anode and cathode should be at least partially transparent to allow the generated light to be observed.

Examples of hole transport materials which may be used for layer 120 have been summarized, for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3, 3'-dimethyl)biphenyl]-4,4'-diamine (ETPD), tetrakis-(3-methylphenyl)-N,N',N'-2,5-phenylenediamine (PDA), a-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino) styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), and porphyrinic compounds, such as copper phthalocyanine. Commonly used hole transporting polymers are polyvinylcarbazole, (phenylmethyl)polysilane, and polyaniline and mixtures thereof. It is also possible to obtain hole transporting polymers by doping hole transporting molecules such as those mentioned above into polymers such as polystyrene and polycarbonate.

Examples of the photoactive layer 130 include all known electroluminescent materials. Organometallic electroluminescent compounds are preferred. The most preferred compounds include cyclometalated iridium and platinum electroluminescent compounds and mixtures thereof. Complexes of Iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications US 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in Synth. Met. (2001), 116 (1-3), 379-383, and Campbell et al., in Phys. Rev. B, Vol. 65 085210. as have been Examples of a few suitable iridium complexes are given in FIG. 7, as Formulae VI(a) through VI(e). Analogous tetradentate platinum complexes can also be used. These electroluminescent complexes can be used alone, or doped into charge-carrying hosts, as noted above. The quinoxaline materials of the present invention may also be used as such charge-carrying hosts in the emissive layer.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and $Li_2O$ can also be deposited between the organic layer and the cathode layer to lower the operating voltage.

It is known to have other layers in organic electronic devices. For example, there can be a layer (not shown) between the anode 110 and hole transport layer 120 to facilitate positive charge transport and/or band-gap matching of the layers, or to function as a protective layer. Layers that are known in the art can be used. In addition, any of the above-described layers can be made of two or more layers. Alternatively, some or all of anode layer 110, the hole transport layer 120, the electron transport layers 140 and 150, and cathode layer 160, may be surface treated to increase charge carrier transport efficiency. The choice of materials for each of the component layers is preferably determined by balancing the goals of providing a device with high device efficiency with device operational lifetime.

It is understood that each functional layer may be made up of more than one layer.

The device can be prepared by a variety of techniques, including sequentially vapor depositing the individual layers on a suitable substrate. Substrates such as glass and polymeric films can be used. Conventional vapor deposition techniques can be used, such as thermal evaporation, chemical vapor deposition, and the like. Alternatively, the organic layers can be applied from solutions or dispersions in suitable solvents, using any conventional coating or printing technique, including but not limited to spin-coating, dip-coating, roll-to-roll techniques, ink-jet printing, screen printing and gravure printing. In general, the different layers will have the following range of thicknesses: anode 110, 500-5000 Å, preferably 1000-2000 Å; hole transport layer 120, 50-2000 Å, preferably 200-1000 Å; photoactive layer 130, 10-2000 Å, preferably 100-1000 Å; electron transport layer 140 and 150, 50-2000 Å, preferably 100-1000 Å; cathode 160, 200-10000 Å, preferably 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

The quinoxaline derivative compounds of the invention may be useful in applications other than OLEDs. For example, these compositions may be used in photovoltaic devices for solar energy conversion. They may also be used in field effect transistor for smart card and thin film transistor (TFT) display driver applications.

EXAMPLES

The following examples illustrate certain features and advantages of the present invention. They are intended to be illustrative of the invention, but not limiting. All percentages are by weight, unless otherwise indicated.

Examples 1-16

These examples illustrate the preparation of quinoxaline derivative ET/AQ compositions.

Example 1

This example illustrates the preparation of Compound I(n) in FIG. 4.

An oven-dried resealable Schlenk flask was charged with 2,3-(bi-4-fluorophenyl)-6-bromoquinoxaline (2.00 g, 5.00 mmol), para-tert-butylstyrene (1.02 g, 6.40 mmol), $Na_2CO_3$ (0.68 g, 6.40 mmol), trans-di(t-acetato)bis[o-(di-o-tolyl-phosphino)benzyl]dipalladium (II) (0.020 g, 0.02 mmol) and 2,6-di-tert-butyl-p-cresol (0.552 g, 2.50 mmol) and N,N-dimethylacetamide (12 mL). The Schlenk flask was sealed with a Teflon valve and the reaction mixture was heated at 130° C. for 21 h. The resulting mixture was cooled to room temperature, diluted in $Et_2O$ (230 mL) and filtered through a pad of silica. The filtrate was washed with water (2×100 mL) and brine (1×50 mL). The organic layer was dried and concentrated to give a crude product which was then purified by flash chromatography to afford the pure product as a light-yellow solid in 72% (1.71 g) yield. $^{19}F$ NMR (376.8 Hz, $CD_2Cl_2$): δ −113.48 and −113.58.

Example 2

This example illustrates the preparation of Compound I(o) in FIG. 4.

An oven-dried resealable Schlenk flask was charged with 4-fluorophenylacetylene (0.334 g, 2.78 mmol), 2,3-(bi-4-fluorophenyl)-6-bromoquinoxaline (1 g, 2.53 mmol), $Pd_2(dba)_3$ (0.046 g, 0.05 mmol), triphenylphosphine (0.066 g, 0.253 mmol), CuI (0.010 g, 0.05 mmol) and triethylamine (15 mL). The flask was then sealed and heated at 60° C. for 24 hours. The reaction mixture was diluted with $CH_2Cl_2$, washed with $H_2O$ and brine, dried over $MgSO_4$, filtered and concentrated to afford an off-white solid. The crude product was purified by repeated washes with hexanes (3×20 mL) to yield 0.924 g (84% yield). $^1H$ NMR ($CD_2Cl_2$, 500 MHz) δ 8.37 (d, 1H, J=1.6), 8.20-8.18 (d, 1H, 8.8), 7.98-7.95 (dd, 1H, J=8.3, 1.5), 7.74-7.70 (dd, 2H, J=5.4, 3.6), 7.64-7.60 (m, 4H), 7.24-7.14 (m, 6H). $^{19}F$ NMR ($CD_2Cl_2$, 500 MHz) δ −111.14 (m, 1F), −113.1 (m, 2F).

Example 3

This example illustrates the preparation of Compound I(q) in FIG. 4.

A reactor was charged with Compound I(n) from Example 1 (1.70 g, 3.55 mmol), ESCAT 140 Pd/C catalyst (0.056 g), and MeOH (45 mL). The reaction mixture was flushed with nitrogen, pressurized to 500 psig H2 and heated up to 60 C for 8 h. The volatiles were removed under vacuum and the product was purified by flash chromatography (5% EtOAc/hexane, where "Et" represents ethyl and "OAc" represents acetate) to yield a light-yellow powder (0.220 g, 13%). $^{19}F$ NMR (376.8 Hz, $CD_2Cl_2$): δ −111.14 and −114.60.

Example 4

This example illustrates the preparation of Compound I(b) in FIG. 4.

A mixture of 3,4-diaminotoluene (28.78 g, 0.236 mol) and benzil (45 g, 0.214 mol) was refluxed in 738 mL chloroform with 2.16 mL trifluoroacetic acid for 3 hours. The mixture was washed 3 times with 10% HCl, brine, and dried over $MgSO_4$, filtered, and then filtered through a silica bed with vacuum. The resultant solution was evaporated to dryness. Recrystallized 69 grams of crude product from 550 mL methanol. Filtered solids were dried in a vacuum oven at 50° C. for 1 hour to yield 55.56 g of dried solid. 78.8% yield

Example 5

This example illustrates the preparation of Compound I(e) in FIG. 4.

A mixture of 3,4-diaminotoluene (4.49 g, 0.037 mol) and 4,4'-dimethoxybenzil (9.46 g, 0.035 mol) was refluxed in 125 mL chloroform with 0.35 mL trifluoroacetic acid for 6 hours. The mixture was washed 2 times with water, dried over $MgSO_4$, and evaporated to −11 g. The solid was dissolved in 1:1 ethyl acetate:chloroform for flash chromatography and eluted with ethyl acetate. Evaporated to 9.7 grams of dark solid. 72% yield

Example 6

This example illustrates the preparation of Compound I(c) in FIG. 4.

A mixture of 3,4-diaminotoluene (0.603 g, 4.93 mmol) and 1,10-phenanthroline-5,6-dione (0.945 g, 4.50 mmol) was refluxed in 602 mL chloroform with 0.35 mL trifluoroacetic acid for 6 hours. The mixture was filtered hot through a medium frit to yield 0.85 g of light yellow solid after drying. Yield 63% A second crop was obtained from mother liquor after cooling to yield an additional 0.31 g.

Example 7

This example illustrates the preparation of Compound I(d) in FIG. 4.

A mixture of 3,4-diaminotoluene (5.36 g, 44 mmol) and phenanthrene quinone (8.33 g, 0.040 mol) was refluxed in 119 mL chloroform with 0.4 mL trifluoroacetic acid for 6 hours. The mixture was filtered through a medium frit and recrystallized from 430 g of methyl ethyl ketone to yield 5.5 g fluffy wool-like, yellow product. 46% yield

Example 8

This example illustrates the preparation of Compound I(f) in FIG. 4.

A mixture of 3,4-diaminotoluene (5.36 g, 44 mmol) and 2,2'-Pyridil (8.49 g, 40 mmol) was refluxed in 119 mL chloroform with 0.4 mL trifluoroacetic acid for 4 hours. The reaction mixture was separated and washed 4 times with 100 mL water, and evaporated to 10.4 g. The resultant solid was dissolved in 1:1 ethyl acetate:chloroform for flash chromatography and eluted with ethyl acetate. Evaporated to yield 9.3 g of solid.

Example 9

This example illustrates the preparation of Compound I(g) in FIG. 4.

A mixture of methyl-3,4-diaminobenzoate (7.28 g, 44 mmol) and benzil (8.41 g, 40 mmol) was refluxed in 140 ml methylene chloride for 21 hours. The reaction mixture was evaporated to dryness and then dissolved in 520 mL methanol and 150 mL methylene chloride at reflux. The solution was then partially evaporated to selectively crystallize the desired product

Example 10

This example illustrates the preparation of Compound I(k) in FIG. 4.

A mixture of Methyl-3,4-diaminobenzoate (6.37 g, 0.038 mol) and 4,4'-dimethoxybenzil (9.46 g, 0.035 mol) was refluxed in 142 mL methylene chloride with 3 drops trifluoroacetic acid for 5 hours. 10.7 g N-methylpyrrolidinone was added and reflux continued for 26 more hours. The mixture was washed 3 times with water, dried over $MgSO_4$, filtered and then precipitated the product be decanting the organic solution into 550 g methanol. After standing overnight, the product was filtered and dried at 95° C. in vacuum to yield 10.39 g product.

Example 11

This example illustrates the preparation of Compound I(r) in FIG. 4.

A mixture of Methyl-3,4-diaminobenzoate (6.12 g, 0.037 mol) and phenanthrene quinone (7.08 g, 0.034 mol) was refluxed in 119 mL methylene chloride. 100 g of N-methylpyrrolidinone was added and the chlorinated solvent was distilled out. The pot was warmed to 150° C. whereupon a clear solution was obtained and the reaction was tracked by gas chromatography. The product was precipitated by pouring into 410 g methanol and the solid precipitate filtered off. The product was recrystallized from toluene then recrystallized again from a combination of methyl ethyl ketone 1200 g, toluene 150 g, and tetrahydrofuran 1100 g. Yield was 3.3 g of pearly golden wool-like material.

Example 12

This example illustrates the preparation of Compound I(l) in FIG. 4.

A mixture of 1,2-phenylenediamine (13.91 g, 0.129 mol) and 4,4'-dibromobenzil (45 g, 0.116 mol) was refluxed in 558 mL chloroform with 1.0 ml trifluoroacetic acid for 6 hours. The mixture was washed 3 times with 10% HCl, and evaporated to ~51 g. Recrystallized from 600 mL ethyl acetate with 100 mL methanol at reflux. Large crystals formed overnight and were filtered and washed with methanol twice and dried to 29.63 g with a 4.9 g second crop from the chilled mother liquor.

Example 13

This example illustrates the preparation of Compound I(h) in FIG. 4.

A mixture of 2,3-diaminotoluene (4.84 g, 0.040 mol) and benzil (7.56 g, 0.036 mol) was refluxed in 112 mL methylene chloride for 19 hours. The mixture was washed 4 times with 12% HCl, and dried over $MgSO_4$ filtered and evaporated to ~9.5 g of brown solid. The solid was dissolved into 495 g methanol at reflux and then ~300 g solvent was distilled out. Cooling with ice yielded nice crystals. Filtered and washed crystal cake with methanol.

Example 14

This example illustrates the preparation of Compound I(i) in FIG. 4.

A mixture of 2,3-diaminotoluene (5.05 g, 0.041 mol) and phenanthrenequinone (7.84 g, 0.038 mol) were refluxed in 112 ml chloroform for 29 hours. The resultant solution was chromatographed down a silica column with chloroform eluant. Evaporated product from solvent to yield about 10 g before vacuum oven drying. Material appeared crystalline

Example 15

This example illustrates the preparation of Compound I(j) in FIG. 4.

A mixture of methyl-3,4-diaminobenzoate (7.28 g 0.044 mol) and 2,2'-pyridil (8.48 g, 0.040 mol) was refluxed in 140 mL methylene chloride for 7 hours. The solution was evaporated to 15.7 g and the solid dissolved in 240 mL methylene chloride and 140 mL methanol at reflux. After addition of 280 mL methanol and evaporation of ~150 mL of the solvent the solution was left to stand overnight. The resulting solid was collected and dried to 9.8 g. Took 7.7 g material and dissolved in 203 g methanol with 50 g methylene chloride. Distilled off >50 mL of solvent. Crystals formed overnight. Filtered and dried in vacuum oven.

Example 16

This example illustrates the preparation of Compound I(t) in FIG. 4.

An oven-dried resealable Schlenk flask was charged with 2,3-(bi-4-fluorophenyl)-6-bromoquinoxaline (1.23 g, 3.08 mmol), 1,3-divinyltetramethyldisiloxane (3.40 mL, 14.8 mmol), KOAc (0.440 g, 4.48 mmol), $Pd(OAc)_2$ (0.012 g, 0.06 mmol), $P(o\text{-Tol})_3$ (0.06 g, 0.20 mmol), $NEt_3$ (0.300 mL), DMF (~2 mL) and water (0.45 mL). The Schlenk flask was sealed with a Teflon valve and the reaction mixture was heated at 95° C. for 48 h. The resulting mixture was cooled to room temperature, diluted in water (15 mL) and the product was extracted with $CH_2Cl_2$ (15 mL). The organic layer was dried and concentrated to give a crude product, which was purified by chromatography (3% EtOAc/hexane) as a light-yellow solid (0.478 g, 31% yield). $^{19}F$ NMR (376.8 Hz, $CD_2Cl_2$): δ –113.45 (br m).

Examples 17-19

These examples illustrate the preparation of charge transport compositions having more than one quinoxaline group.

Example 17

This example illustrates the preparation of Compound II(d) in FIG. 6.

A 3-necked 500 mL round bottomed flask fitted with a nitrogen inlet and a condensor was charged with 1,4-phenylenebisboronic acid (2 g, 12.1 mmol), 2,3-(bi-4-fluorophenyl)-6-bromoquinoxaline (9.54 g, 24.1 mmol), $Pd(PPh_3)_4$ (2.78 g, 2.41 mmol), potassium carbonate (6.67 g, 48.3 mmol), DME (150 mL) and $H_2O$ (150 mL). The reaction mixture was refluxed for 24 h, after which it was diluted with $H_2O$ and $CH_2Cl_2$. The organic layer contained a precipitate, which was isolated by filtration and washed with $CH_2Cl_2$ to yield 2.75 g (32% yield) of an off-white powder. $^1H$ NMR ($CD_2Cl_2$, 500 MHz) δ 8.56-8.55 (m, 2H), 8.35-8.33 (d, 2H), 8.29 (m, 2H), 8.12 (s, 4H), 7.68-7.64 (m, 8H), 7.29-7.16 (m, 8H). $^{19}F$ NMR ($CD_2Cl_2$, 500 MHz) δ –113.35 (m, 2F).

Example 18

This example illustrates the preparation of Compound II(j) in FIG. 6.

A mixture of 1,4-bisbenzil (1 g, 2.92 mmol) and 4,5-dimethyl-1,2-phenylenediamine (0.769 g, 5.84 mmol) in chloroform (20 mL) was refluxed for 15 hrs under an atmosphere of nitrogen. Hexanes was added to reaction mixture, precipitating out a bright yellow precipitate which was isolated by filtration and washed with hexanes to yield the product as a bright-yellow powder (1.32 g, 83% yield). $^1H$ NMR ($CD_2Cl_2$, 500 MHz) δ 7.89-7.88 (d, 4H, J=7.1 Hz), 7.50-7.48 (dd, 4H, J=1.5 Hz, 7.7 Hz), 7.45 (s, 4H), 7.35-7.31 (m, 10H), 2.53 (s, 12H).

Example 19

This example illustrates the preparation of Compound II(a) in FIG. 6.

A mixture of 3,3-diaminobenzidine (0.4580 g, 2.14 mmol) and 1,10-phenanthroline-5,6-dione (0.9458 g, 4.5 mmol) was heated at 85° C. in 10 g N-methylpyrrolidinone with 0.045 ml trifluoroacetic acid for 23 hours. At ambient temperature chloroform was charged to the pot and the contents were filtered through a fine frit and washed with acetone, and diethylether then dried at 90° C. and vacuum.

Example 20

This example illustrates the preparation of Compound I(m) in FIG. 4.

The synthesis of this compound was carried out following the synthetic method used for the preparation of I(o) to give the desired product in 58% yield. $^1$H NMR (CD$_2$Cl$_2$, 500 MHz) δ 8.38 (d, 1H, J=1.8 Hz), 8.20-8.18 (d, 1H, 8.4 Hz), 7.99-7.97 (dd, 1H, J=1.8 Hz, 8.7 Hz), 7.73-7.71 (m, 2H), 7.64-7.61 (m, 4H), 7.52-7.50 (m, 3H), 7.19-7.14 (m, 4H). $^{19}$F NMR (CD$_2$Cl$_2$, 500 MHz) δ −113.14 (m, 2F).

Example 21

This example illustrates the preparation of Compound II(f) in FIG. 6.

The synthesis of this compound was carried out following the synthetic method used for the preparation of II(e) to give the desired product in 13% yield. $^1$H NMR (CD$_2$Cl$_2$, 500 MHz) δ 8.42-8.41 (d, 2H, J=1.9), 8.20-8.18 (d, 2H, J=8.5), 8.13-8.11 (dd, 2H, J=9.1 Hz, 2.0 Hz), 8.00 (s, 4H), 7.54-7.51 (dd, 8H, J=8.7 Hz, 3.1 Hz), 6.9-6.9 (q, 8H), 5.48 (s, 12H).

Example 22

This example illustrates the preparation of Compound II(c) in FIG. 6.

The synthesis of this compound was carried out following the synthetic method used for the preparation of II(e) to give the desired product in 10% yield. $^1$H NMR (CD$_2$Cl$_2$, 500 MHz) δ 8.62-8.61 (d, 2H, J=1.5), 8.44-8.41 (m, 4H), 8.41-8.39 (d, 2H, J=9.5 Hz), 8.34-8.31 (dd, 2H, J=8.3 Hz, 1.6 Hz), 8.14 (m, 6H), 8.12-8.11 (m, 2H), 7.98-7.94 (m, 4H), 7.38-7.34 (m, 4H).

Example 23

This example illustrates the preparation of Compound II(j) in FIG. 6.

The synthesis of this compound was carried out following the synthetic method used for the preparation of II(j) to give the desired product in 66% yield. $^1$H NMR (CD$_2$Cl$_2$, 500 MHz) δ 8.09-8.06 (t, 2H, J=7.4 Hz), 7.98-7.96 (d, 2H, J=7.2 Hz), 7.69-7.67 (d, 2H, 8.9), 7.59-7.51 (m, 10H), 7.43-7.40 (m, 8H), 2.67 (s, 6H).

Example 24

This example illustrates the preparation of Compound II(k) in FIG. 6.

The synthesis of this compound was carried out following the synthetic method used for the preparation of II(j) to give the desired product in 65% yield. $^1$H NMR (CD$_2$Cl$_2$, 500 MHz) δ 8.29-8.24 (m, 1H), 8.07-8.01 (m, 1H), 7.90-7.86 (m, 1H), 7.80-7.78 (m, 0.6H), 7.72-7.66 (m, 1H), 7.64-7.59 (m, 4H), 7.51-7.44 (m, 3H). $^{19}$F NMR (CD$_2$Cl$_2$, 500 MHz) δ −108.4 (m, 2F), −108.9 (m, 3F), −109.2 (m, 8F), −109.4 (m, 8F).

Example 25

This example illustrates the preparation of Compound II(1) in FIG. 6.

The synthesis of this compound was carried out using the synthetic scheme shown below.

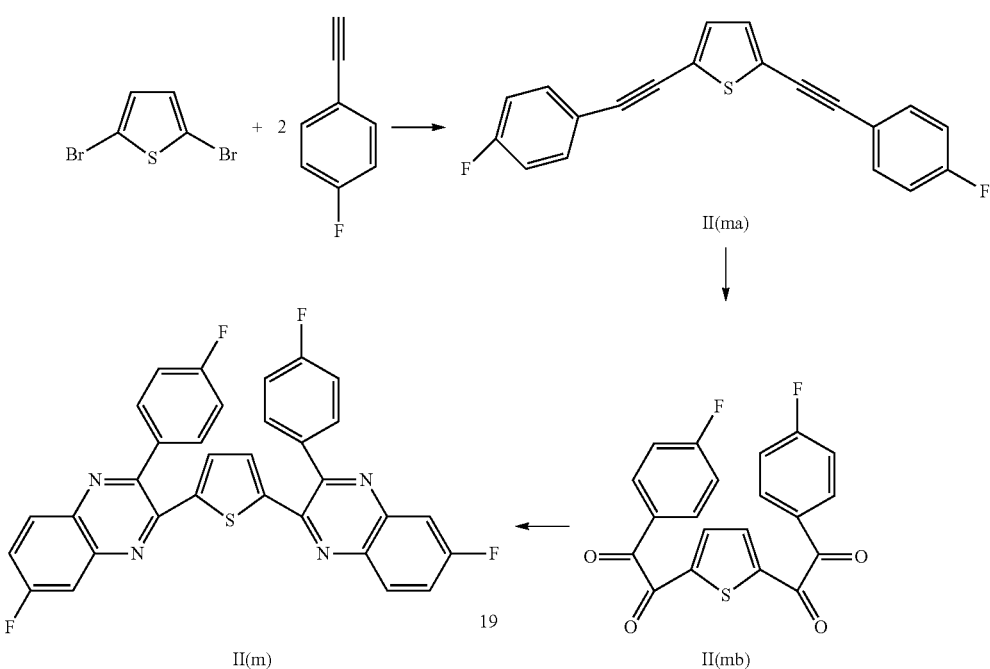

Compound II(ma) was obtained using the synthetic method used for I(o) to produce the expected product in 65% yield. $^1$H NMR (CD$_2$Cl$_2$, 500 MHz) δ 7.64-7.60 (m, 4H), 7.27 (s, 2H), 7.20-7.16 (t, 4H, J=8.9 Hz). $^{19}$F NMR (CD$_2$Cl$_2$, 500 MHz) δ −111.10 (m, 2F). Under nitrogen, a three-necked round bottomed flask fitted with a condensor was charged with II(ma) (2.00 g, 6.25 mmol, 0.1 equiv.), Adogen 464 (0.125 g), potassium permanganate (4.9 g, 31.25 mmol, 5.00 equiv.), sodium bicarbonate (1.05 g, 12.5 mmol, 2.0 equiv.), H$_2$O (80 mL) and CH$_2$Cl$_2$ (50 mL). The mixture was allowed to reflux for 36 hours. After cooling to room temperature, 9.3 g sodium bicarbonate and 4 mL HCl were slowly added to the reaction mixture to neutralize and remove any excess oxidizing agents. The reaction mixture was then diluted with dichloromethane and H$_2$O, the layers separated and the organic portion washed with H$_2$O, brine and dried over MgSO$_4$. The product was isolated by evaporating the solvent and then was recrystallized from ethanol to give 0.6 g (25% yield) of II(mb) as yellow needle-like crystals. $^1$H NMR (CD$_2$Cl$_2$, 500 MHz): δ 8.25-8.21 (dd, 4H, J=8.9 Hz, 5.6 Hz), 7.98 (s, 2H), 7.36-7.32 (t, 4H, J=8.70 Hz). $^{19}$F NMR (CD$_2$Cl$_2$, 500 MHz): δ −101.8 (m, 2F). The synthesis of compound II(m) was carried out following the procedure used for the preparation of II(k) to give the desired product in 20% yield. $^1$H NMR (CD$_2$Cl$_2$, 500 MHz) δ 8.25-8.21 (m, 1H), 8.19-8.15 (m, 1H), 7.85-7.78 (m, 2H), 7.73-7.64 (m, 6H), 7.29-7.25 (t, 4H), 6.69-6.66 (m, 2H). $^{19}$F NMR (CD$_2$Cl$_2$ 500 MHz) δ −108.7, −108.8 (m, 2F), −112.4 (m, 1F), −112.6 (m, 1F).

The properties of the electron transport and/or anti-quenching compositions are summarized in Table 1 below.

TABLE 1

Properties

| Compounds | Absorption onset (nm), E1-E5 | Absorption maximum (nm) | $E_{1/2}$ vs SCE (volt), | LUMO vs vacuum (eV), E1 |
|---|---|---|---|---|
| Compound I(a) | 375 | 345 | −1.5 | −3.33 |
| Compound I(b) | 378 | 339 | −1.6 | −3.24 |
| Compound I(c) | 400 | 385 | −1.17 | −3.67 |
| Compound I(d) | 410 | 397 | −1.3 | −3.54 |
| Compound I(g) | 390 | 352 | −1.29 | −3.55 |
| Compound II(a) | — | — | — | — what is the purpose of this line? |
| Compound I(e) | 405 | 369 | −1.66 | −3.18 |
| Compound I(f) | 378 | 339 | −1.53 | −3.31 |
| Compound I(o) | 420 | 382 | −1.35 | −3.49 |
| Compound I(l) | 407 | 394 | −1.28 | −3.56 |
| Compound I(k) | 385 | 343 | −1.59 | −3.25 |
| Compound I(w) | 417 | 401 | −1.03 | −3.81 |
| Compound I(p) | 380 | 347 | −1.49 | −3.35 |
| Compound I(x) | 380 | 342 | −1.22 | −3.62 |
| Comp. A DDPA | 368 | 310 | −1.85 | −2.99 |
| Comp. B DPA | 366 | 316 | −1.95 | −2.89 |

Example 27

This example illustrates the preparation of an iridium electroluminescent complex, shown as Formula V(a) in FIG. 7. Phenylpyridine ligand, 2-(4-fluorophenyl)-5-trifluoromethylpyridine The general procedure used was described in O. Lohse, P. Thevenin, E. Waldvogel *Synlett,* 1999, 45-48. A mixture of 200 ml of degassed water, 20 g of potassium carbonate, 150 ml of 1,2-dimethoxyethane, 0.5 g of Pd(PPh$_3$)$_4$, 0.05 mol of 2-chloro-5-trifluoromethylpyridine and 0.05 mol of 4-fluorophenylboronic acid was refluxed (80-90° C.) for 16-30 h. The resulting reaction mixture was diluted with 300 ml of water and extracted with CH$_2$Cl$_2$ (2×100 ml). The combined organic layers were dried over MgSO$_4$, and the solvent removed by vacuum. The liquid products were purified by fractional vacuum distillation. The solid materials were recrystallized from hexane. The typical purity of isolated materials was >98%.

Iridium Complex:

A mixture of IrCl$_3$.nH$_2$O (54% Ir; 508 mg), 2-(4-fluorophenyl)-5-trifluoromethylpyridine, from above (2.20 g), AgOCOCF$_3$ (1.01 g), and water (1 mL) was vigorously stirred under a flow of N$_2$ as the temperature was slowly (30 min) brought up to 185° C. (oil bath). After 2 hours at 185-190° C. the mixture solidified. The mixture was cooled down to room temperature. The solids were extracted with dichloromethane until the extracts decolorized. The combined dichloromethane solutions were filtered through a short silica column and evaporated. After methanol (50 mL) was added to the residue the flask was kept at −10° C. overnight. The yellow precipitate of the tris-cyclometalated complex, compound V(a) in FIG. 7A, was separated, washed with methanol, and dried under vacuum. Yield: 1.07 g (82%). X-Ray quality crystals of the complex were obtained by slowly cooling its warm solution in 1,2-dichloroethane.

Example 28

This example illustrates the formation of OLEDs using the charge transport compositions of the invention.

Thin film OLED devices including a hole transport layer (HT layer), electroluminescent layer (EL layer) and at least one electron transport and/or anti-quenching layer (ET/AQ layer) were fabricated by the thermal evaporation technique. An Edward Auto 306 evaporator with oil diffusion pump was used. The base vacuum for all of the thin film deposition was in the range of 10$^{-6}$ torr. The deposition chamber was capable of depositing five different films without the need to break up the vacuum.

Patterned indium tin oxide (ITO) coated glass substrates from Thin Film Devices, Inc was used. These ITO's are based on Corning 1737 glass coated with 1400 Å ITO coating, with sheet resistance of 30 ohms/square and 80% light transmission. The patterned ITO substrates were then cleaned ultrasonically in aqueous detergent solution. The substrates were then rinsed with distilled water, followed by isopropanol, and then degreased in toluene vapor for ~3 hours.

The cleaned, patterned ITO substrate was then loaded into the vacuum chamber and the chamber was pumped down to 10$^{-6}$ torr. The substrate was then further cleaned using an oxygen plasma for about 5-10 minutes. After cleaning, multiple layers of thin films were then deposited sequentially onto the substrate by thermal evaporation. Finally, patterned metal electrodes of Al or LiF and Al were deposited through a mask. The thickness of the film was measured during deposition using a quartz crystal monitor (Sycon STC-200). All film thickness reported in the Examples are nominal, calculated assuming the density of the material deposited to be one. The completed OLED device was then taken out of the vacuum chamber and characterized immediately without encapsulation.

Table 2 summarizes the devices made with the quinoxaline derivative ET/AQ compositions of the invention. In all cases the anode was ITO, as discussed above, the hole transport layer was MPMP, and the emitting layer was the iridium complex from Example 27, having the thicknesses indicated. When present, electron transport layer 150 was tris(8-hydroxyquinolato)aluminum(III), Alq, having the thicknesses given. The cathode was a layer of Al or a dual layer of LiF/Al, with the thicknesses given.

TABLE 2

Devices

| Sample | HT (Å) | EL, Å | ET/AQ, Å | ET, Å | Cathode, Å |
|---|---|---|---|---|---|
| Comparative A | 507 | 407 | Comp. A 408 | | Al 721 |
| Comparative B | 507 | 405 | Comp. B 407 | | Al 732 |
| 3-1 | 545 | 403 | I(a) 430 | Alq 430 | Al 737 |
| 3-2 | 508 | 625 | I(b) 425 | | Al 732 |
| 3-3 | 509 | 413 | I(c) 416 | | Al 750 |
| 3-4 | 578 | 411 | I(d) 381 | | Al 711 |
| 3-5 | 527 | 418 | I(e) 418 | | Al 1027 |
| 3-6 | 535 | 415 | I(f) 459 | | Al 1039 |
| 3-7 | 549 | 425 | I(g) 423 | | Al 1023 |
| 3-8 | 510 | 445 | II(a) 415 | | Al 710 |
| 3-9 | 502 | 403 | I(f) 106 | Alq 303 | LiF 5 Al 470 |
| 3-10 | 502 | 402 | I(d) 102 | Alq 303 | LiF 5 Al 497 |
| 3-11 | 501 | 402 | I(c) 103 | Alq 302 | LiF 5 Al 111 |
| 3-12 | 513 | 409 | I(h) 414 | | Al 718 |
| 3-13 | 514 | 416 | I(i) 408 | | Al 718 |
| 3-14 | 515 | 500 | I(i) 410 | | Al 729 |
| 3-15 | 504 | 488 | I(j) 402 | | Al 721 |
| 3-16 | 505 | 412 | I(k) 439 | | Al 727 |
| 3-17 | 516 | 409 | I(l) 432 | | Al 733 |
| 3-18 | 302 | 403 | II(c) 102 | Alq 302 | LiF 10 Al 452 |
| 3-19 | 304 | 402 | II(d) 101 | Alq 302 | LiF 10 Al 452 |
| 3-20 | 305 | 404 | II(e) 102 | Alq 303 | LiF 10 Al 454 |
| 3-21 | 301 | 402 | II(f) 105 | Alq 305 | LiF 10 Al 451 |
| 3-22 | 303 | 406 | I(m) 103 | Alq 302 | LiF 10 Al 453 |
| 3-23 | 303 | 405 | II(g) 102 | Alq 305 | LiF 10 Al 453 |
| 3-24 | 304 | 402 | I(n) 101 | Alq 303 | LiF 10 Al 453 |
| 3-25 | 303 | 410 | II(h) 102 | Alq 305 | LiF 10 Al 453 |
| 3-26 | 306 | 404 | I(o) 103 | Alq 302 | LiF 10 Al 453 |

TABLE 2-continued

Devices

| Sample | HT (Å) | EL, Å | ET/AQ, Å | ET, Å | Cathode, Å |
|---|---|---|---|---|---|
| 3-27 | 305 | 404 | II(i) 192 | Alq 305 | LiF 10 Al 453 |
| 3-28 | 303 | 402 | I(p) 102 | Alq 304 | LiF 10 Al 456 |
| 3-29 | 303 | 403 | II(j) 103 | Alq 303 | LiF 10 Al 335 |
| 3-30 | 303 | 405 | II(k) 102 | Alq 305 | LiF 10 Al 284 |
| 3-31 | 303 | 405 | II(l) 102 | Alq 303 | LiF 10 Al 232 |

Figure 9:
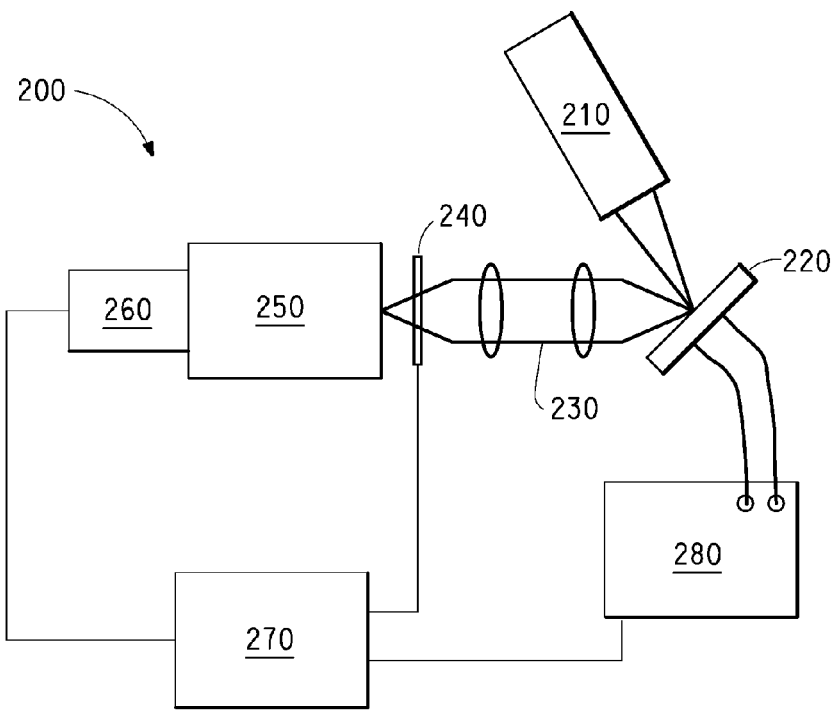
FIG. 9 is a schematic diagram of a testing device for an LED.
Figure 10A:
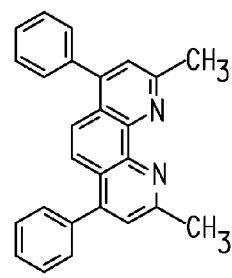
FIG. 10 shows formulae for known electron transport compositions.
Figure 10B:
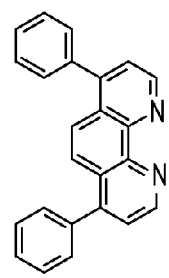

The OLED samples were characterized by measuring their (1) current-voltage (I-V) curves, (2) electroluminescence radiance versus voltage, and (3) electroluminescence spectra versus voltage. The apparatus used, 200, is shown in FIG. 9. The I-V curves of an OLED sample, 220, were measured with a Keithley Source-Measurement Unit Model 237, 280. The electroluminescence radiance (in the unit of $cd/m^2$) vs. voltage was measured with a Minolta LS-110 luminescence meter, 210, while the voltage was scanned using the Keithley SMU. The electroluminescence spectrum was obtained by collecting light using a pair of lenses, 230, through an electronic shutter, 240, dispersed through a spectrograph, 250, and then measured with a diode array detector, 260. All three measurements were performed at the same time and controlled by a computer, 270. The efficiency of the device at certain voltage is determined by dividing the electroluminescence radiance of the LED by the current density needed to run the device. The unit is in cd/A.

The results for devices using the quinoxaline derivative ET/AQ compositions of the invention are given in Table 3 below:

TABLE 3

Electroluminescent Properties of Devices

| Sample | Peak Radiance, cd/m2 | Efficiency at Peak Radiance cd/A | Peak efficiency, cd/A | Peak power efficiency lm/W |
|---|---|---|---|---|
| Comp. F | 3000 at 22 V | 10 | 14 | |
| Comp. G | 4500 at 19 V | 10 | 20 | |
| 3-1 | 2300 at 20 V | 4 | 5.4 | |
| 3-2 | 2700 at 27 V | | 10 | |
| 3-3 | 4000 at 15 V | | 10-16 | |
| 3-4 | 90 at 22 V | | 4.4 | |
| 3-5 | 200 at 22 V | | 1.1 | |
| 3-6 | 2500 at 21 V | | 8.5 | |
| 3-7 | 2000 at 22 V | | 13 | |
| 3-8 | 290 at 16 V | | 1.8 | |
| 3-9 | 7000 at 15 V | | 30 | 15 |
| 3-10 | 1000 at 25 V | | 14 | |
| 3-11 | 6500 at 15 V | | 26 | |

TABLE 3-continued

Electroluminescent Properties of Devices

| Sample | Peak Radiance, cd/m2 | Efficiency at Peak Radiance cd/A | Peak efficiency, cd/A | Peak power efficiency lm/W |
|---|---|---|---|---|
| 3-12 | 1200 at 20 V | | 9.5 | |
| 3-13 | 300 at 19 V | | 2.6 | |
| 3-14 | 220 at 26 V | | 2.6 | |
| 3-15 | 180 at 25 V | | 8.5 | |
| 3-16 | 1600 at 22 V | | 11 | |
| 3-17 | 100 at 22 V | | 1.2 | |
| 3-18 | 4200-5800 at 15 V | | 16-20 | |
| 3-19 | 4000-5000 at 15 V | | 17-20 | |
| 3-20 | 4800-5400 at 17 V | | 15-17 | |
| 3-21 | 2300 at 20 V | | 10.5 | |
| 3-22 | 4000 at 17 V | | 15-19 at 13 V | |
| 3-23 | 5000 at 17 V | | 17-22 at 13 V | |
| 3-24 | 5600 at 17 V | | 22 at 14 V | |
| 3-25 | 1400 at 17 V | | 5.5 at 13 V | |
| 3-26 | 8000 at 14 V | | 20 at 11 V | |
| 3-27 | 7000 at 17 V | | 16 at 14 V | |
| 3-28 | 6000 at 15 V | | 15-20 at 14-11 V | |
| 3-29 | 6500 at 16 V | | 18 at 13 V | |
| 3-30 | 6500 at 15 V | | 19 at 11 V | |
| 3-31 | 6000 at 16 V | | 14 at 12 V | |

What is claimed is:

1. An electronic device comprising a photoactive layer and a second layer, wherein at least one layer comprises a quinoxaline derivative of Formula III:

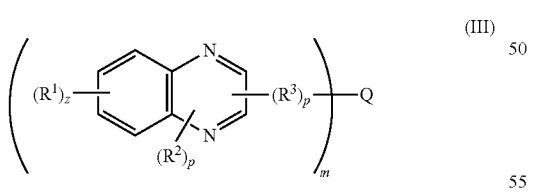

(III)

wherein $R^1$ is selected from alkylacetate groups;
$R^2$ is the same or different at each occurrence and is selected from aryl, heteroaryl, alkylaryl, alkenylaryl, alkynylaryl, alkylheteroaryl, alkenylheteroaryl, alkynylheteroaryl, $C_6H_cF_d$, and $OC_6H_cF_d$;
$R^3$ is the same or different at each occurrence and is selected from a single bond and a group selected from alkylene, heteroalkylene, arylene, heteroarylene, arylenealkylene, and heteroarylenealkylene;
Q is selected from a multiple-ring aromatics, multiple-ring heteroaromatics, fused-ring aromatics, fused-ring heteroaromatics, groups having Formula IV(c), groups having Formula IV(d), and groups having Formula IV(e);

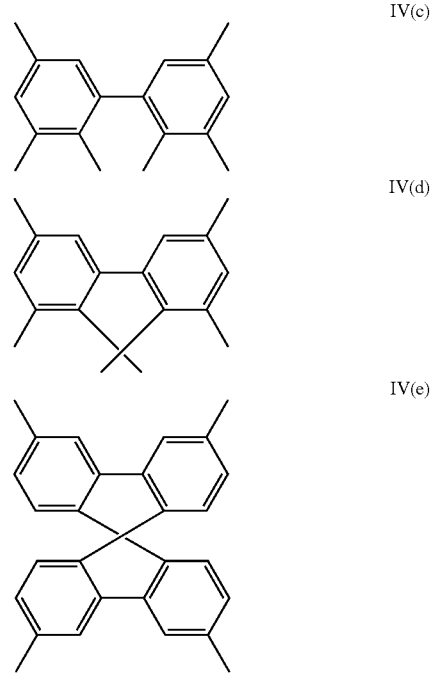

IV(c)

IV(d)

IV(e)

c and d are 0 or an integer such that c+d=5;
m is an integer equal to at least 2;
p is 0 or 1; and
z is 0 or an integer from 1 through 3.

2. An electronic device of claim 1, wherein the device is a light-emitting diode, light-emitting electrochemical cell, or a photodetector.

3. The device of claim 1, wherein $R^2$ is selected from phenyl groups, substituted phenyl groups, pyridyl groups, and substituted pyridyl groups.

4. An electronic device comprising a photoactive layer and a second layer, wherein at least one layer comprises a quinoxaline derivative of Formula III:

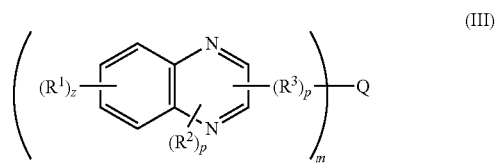

(III)

wherein:
$R^1$ is the same or different at each occurrence and is selected from H, F, Cl, Br, alkyl, heteroalkyl, alkenyl, alkynyl, aryl, heteroaryl, alkylaryl, alkenylaryl, alkynylaryl, alkylheteroaryl, alkenylheteroaryl, alkynylheteroaryl, $C_nH_aF_b$, and $OC_nH_aF_b$;
$R^2$ is the same or different at each occurrence and is selected from aryl, heteroaryl, alkylaryl, alkenylaryl, alkynylaryl, alkylheteroaryl, alkenylheteroaryl alkynylheteroaryl, $C_6H_cF_d$ and $OC_6H_cF_d$;
$R^3$ is selected from aryl, heteroaryl, alkyl, and heteroalkyl;

Q is selected from a multiple-ring aromatics, multiple-ring heteroaromatics, fused-ring aromatics, fused-ring heteroaromatics, groups having Formula IV(c), groups haying Formula IV(d), and groups haying Formula IV(e);

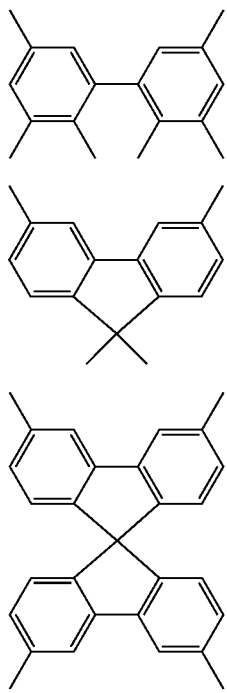

a, b, c and d are 0 or an integer such that a+b=2n+1, and c+d=5;
m is an integer equal to at least 2;
n is an integer;
p is 0 or 1; and
z is 0 or an integer from 1 through 3.

5. The device of claim 4, wherein $R^3$ is selected from phenyl and substituted phenyl.

6. The device of claim 4, wherein $R^3$ is selected from alkyl and heteroalkyl having from 1 to 12 carbon atoms.

7. An electronic device of claim 6, wherein the device is a light-emitting diode, light-emitting electrochemical cell, or a photodetector.

8. The device of claim 4, wherein $R^1$ is selected from alkyl groups having from 1 to 12 carbon atoms.

9. The device of claim 4, wherein $R^2$ is selected from phenyl groups, substituted phenyl groups, pyridyl groups, and substituted pyridyl groups.

10. An electronic device comprising a photoactive layer and a second layer, wherein at least one layer comprises a quinoxaline derivative of Formula III:

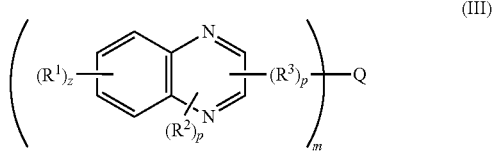

wherein:
$R^1$ is the same or different at each occurrence and is selected from H, F, Cl, Br, alkyl, heteroalkyl, alkenyl, alkynyl, aryl, heteroaryl, alkylaryl, alkenylaryl, alkynylaryl, alkylheteroaryl, alkenylheteroaryl alkynylheteroaryl, $C_nH_aF_b$, and $OC_nH_aF_b$;

$R^2$ is the same or different at each occurrence and is selected from aryl, heteroaryl, alkylaryl, alkenylaryl, alkynylaryl, alkylheteroaryl, alkenylheteroaryl, alkynylheteroaryl, $C_6H_cF_d$, and $OC_6H_cF_d$;

$R^3$ is the same or different at each occurrence and is selected from a single bond and a group selected from alkylene, heteroalkylene, arylene, heteroarylene, arylenealkylene, and heteroaryleneakylerne;

Q is selected from Formulae IV(c)-IV(e)

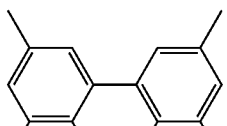

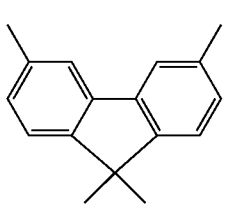

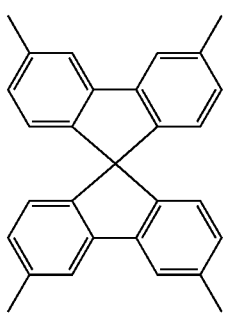

a, b, c and d are 0 or an integer such that a+b=2n+1, and c+d=5;

m is an integer equal to at least 2;

n is an integer;

p is 0 or 1; and z is 0 or an integer from 1 through 3.

11. An electronic device of claim 10, wherein the device is a light-emitting diode, light-emitting electrochemical cell, or a photodetector.

12. The device of claim 10, wherein $R^1$ is selected from alkyl groups having from 1 to 12 carbon atoms.

13. The device of claim 10, wherein $R^2$ is selected from phenyl groups, substituted phenyl groups, pyridyl groups, and substituted pyridyl groups.

* * * * *